United States Patent
Lampert et al.

(10) Patent No.: US 12,402,950 B2
(45) Date of Patent: Sep. 2, 2025

(54) SYSTEM METHOD AND COMPUTER PROGRAM PRODUCT, FOR COMPUTER AIDED SURGERY

(71) Applicant: PATHKEEPER SURGICAL LTD, Rehovot (IL)

(72) Inventors: Erez Lampert, Rehovot (IL); Opher Kinrot, Ra'anana (IL)

(73) Assignee: PATHKEEPER SURGICAL LTD, Rehovot (IL)

( * ) Notice: Subject to any disclaimer, the term of this patent is extended or adjusted under 35 U.S.C. 154(b) by 489 days.

(21) Appl. No.: 17/259,023

(22) PCT Filed: Jul. 11, 2019

(86) PCT No.: PCT/IL2019/050775
§ 371 (c)(1),
(2) Date: Jan. 8, 2021

(87) PCT Pub. No.: WO2020/012479
PCT Pub. Date: Jan. 16, 2020

(65) Prior Publication Data
US 2021/0290315 A1 Sep. 23, 2021

Related U.S. Application Data

(60) Provisional application No. 62/696,882, filed on Jul. 12, 2018.

(51) Int. Cl.
*A61B 34/20* (2016.01)
*A61B 90/00* (2016.01)

(52) U.S. Cl.
CPC ...... *A61B 34/20* (2016.02); *A61B 2034/2048* (2016.02); *A61B 2034/2057* (2016.02);
(Continued)

(58) Field of Classification Search
CPC . A61B 34/20; A61B 34/10; A61B 2034/2048; A61B 2034/2057;
(Continued)

(56) References Cited

U.S. PATENT DOCUMENTS 5,251,127 A 10/1993 Raab
6,021,343 A 2/2000 Foley et al.
(Continued)

FOREIGN PATENT DOCUMENTS

CN 105377175 A 3/2016
CN 106214256 A * 12/2016
(Continued)

OTHER PUBLICATIONS

'Infrared'. Wikipedia [online]. 2017. [retrieved on Feb. 8, 2024]. Retrieved from the internet. <URL https://web.archive.org/web/20170121044409/https://en.wikipedia.org/wiki/Infrared> (Year: 2017).*
(Continued)

*Primary Examiner* — Sean D Mattson
(74) *Attorney, Agent, or Firm* — FisherBroyles, LLP; Roger L. Browdy; Ronni S. Jillions

(57) ABSTRACT

A computerized method aiding a surgeon end-user, comprising Providing a light projector configured to project at least one pattern onto spine, Providing 3D video cameras operative, when the spine is in their field of view, to capture 3D video imagery of the spine and pattern; Providing a tool tracker comprising an INS operative to repeatedly compute an output tool-status indication of a current orientation and position of tool used during spine surgery, and a wireless communication module providing data communication between subsystem and a processor including sending the output tool-status indication to the processor, the processor including logic configured to receive the output tool-status indication generated by the tool tracker and the 3D video
(Continued)

imagery, and to track vertebra, using the pattern, which is known to the processor, and accordingly to provide feedback to the surgeon.

20 Claims, 10 Drawing Sheets

(52) U.S. Cl.
CPC ....... *A61B 2034/2065* (2016.02); *A61B 90/36* (2016.02); *A61B 2090/363* (2016.02); *A61B 2090/366* (2016.02)

(58) Field of Classification Search
CPC ...... A61B 2034/2065; A61B 2090/363; A61B 2090/366; A61B 2090/0807; A61B 2090/371; A61B 2090/373; A61B 6/5247; A61B 6/032; A61B 90/30; A61B 17/1671
See application file for complete search history.

(56) References Cited

U.S. PATENT DOCUMENTS

| | | | |
|---|---|---|---|
| 7,166,114 B2 | 1/2007 | Moctezuma De La Barrera et al. | |
| 7,771,436 B2 | 8/2010 | Moctezuma De La Barrera et al. | |
| 7,974,677 B2* | 7/2011 | Mire | G16H 50/50 600/407 |
| 2001/0036245 A1 | 11/2001 | Kienzle, III et al. | |
| 2004/0092932 A1* | 5/2004 | Aubin | A61B 17/1757 606/279 |
| 2004/0171924 A1 | 9/2004 | Mire et al. | |
| 2005/0059885 A1 | 3/2005 | Melkent et al. | |
| 2005/0195587 A1* | 9/2005 | Moctezuma De La Barrera | A61B 90/35 362/5 |
| 2005/0267354 A1* | 12/2005 | Marquart | A61B 90/36 600/407 |
| 2010/0030232 A1* | 2/2010 | Zehavi | A61F 2/4611 606/130 |
| 2013/0060146 A1* | 3/2013 | Yang | G01B 11/25 600/476 |
| 2014/0107471 A1 | 4/2014 | Haider et al. | |
| 2014/0134586 A1* | 5/2014 | Stein | A61B 34/20 434/262 |
| 2014/0171792 A1* | 6/2014 | Dalal | A61B 17/3403 600/424 |
| 2014/0275981 A1* | 9/2014 | Selover | A61B 5/061 600/424 |
| 2015/0182293 A1* | 7/2015 | Yang | A61B 17/1703 600/424 |
| 2015/0300816 A1* | 10/2015 | Yang | A61B 90/35 356/601 |
| 2015/0313566 A1* | 11/2015 | Diers | A61B 6/505 378/63 |
| 2016/0166333 A1 | 6/2016 | Wang et al. | |
| 2016/0191822 A1* | 6/2016 | Kosugou | G06V 10/143 382/118 |
| 2016/0191887 A1 | 6/2016 | Casas | |
| 2016/0324580 A1 | 11/2016 | Esterberg | |
| 2017/0027651 A1 | 2/2017 | Esterberg | |
| 2018/0042619 A1* | 2/2018 | Frey | A61B 17/151 |
| 2018/0071029 A1 | 3/2018 | Srimohanarajah et al. | |
| 2019/0046275 A1* | 2/2019 | Winneberger | A61B 5/349 |
| 2019/0090955 A1* | 3/2019 | Singh | A61B 17/00 |
| 2019/0388099 A1* | 12/2019 | Zuhars | A61B 90/39 |

FOREIGN PATENT DOCUMENTS

| | | |
|---|---|---|
| CN | 107847278 A | 3/2018 |
| EP | 3332730 A1 | 6/2018 |
| WO | 2017151734 A1 | 9/2017 |
| WO | 2018/076094 A1 | 5/2018 |

OTHER PUBLICATIONS www.chortho.com/education/spine-animations, Aug. 5, 2020, p. 1.
docs.opencv.org/3.1.0/d5/dae/tutorial_aruco_detection.html, Detection of ArUco Markers, Jun. 10, 2019, pp. 1-11.
Kim, et al. Minimally invasive spinal surgery with intraoperative image-guided navigation, BioMed research international, 2016.
open3d.org/docs/release/tutorial/Advanced/multiway_registration. html, Multiway registration, Jul. 14, 2019, pp. 1-7.
Tiouririne, M., et al. Imaging performance of a handheld ultrasound system with real-time computer-aided detection of lumbar spine anatomy: A feasibility study. Investigative radiology, Aug. 2017, pp. 447-455, 52(8).
Zhou, et al., Geometrical dimensions of the lower lumbar vertebrae-analysis of data from digitised CT images. European Spine Journal, 2000, pp. 242-248, 9(3).

* cited by examiner

Fig. 9a
Fig. 9b
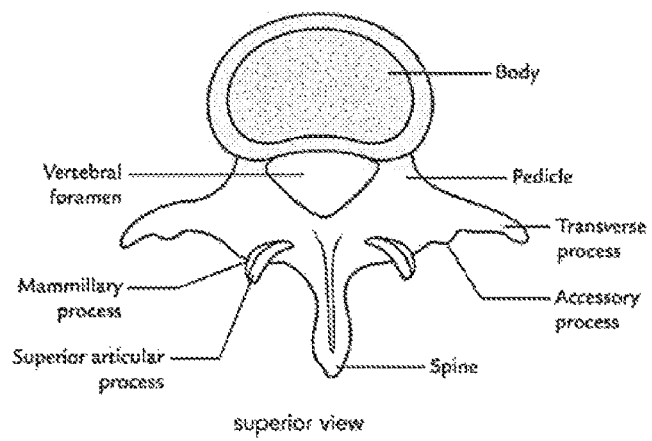
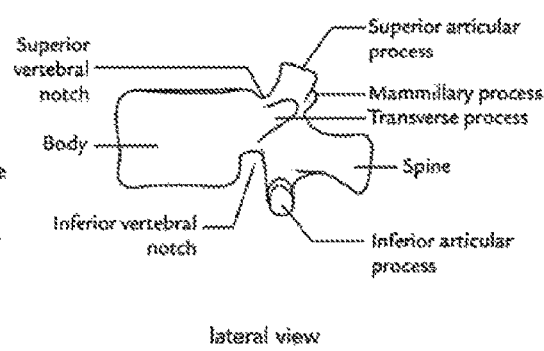
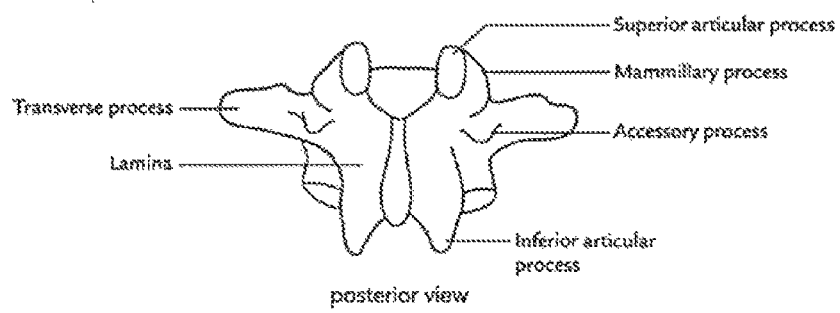
Fig. 9c

SYSTEM METHOD AND COMPUTER PROGRAM PRODUCT, FOR COMPUTER AIDED SURGERY

REFERENCE TO CO-PENDING APPLICATIONS

Priority is claimed from U.S. provisional application No. 62/696,882, entitled "System and Method For Computer Aided Surgery" and filed 12 Jul. 2018, the disclosure of which application/s is hereby incorporated by reference.

FIELD OF THIS DISCLOSURE

The present invention relates generally to surgery and more particularly to computer-aided surgery.

BACKGROUND FOR THIS DISCLOSURE

The state of the art includes "Computer-aided surgery apparatus—U.S. Pat. No. 5,251,127" "Image guided screwdriver—U.S. Pat. No. 6,021,343 B2; U.S. 2001/0036245, which is directed towards a surgical tool, and "Surgical navigation tracker, system and method U.S. Pat. No. 7,771,436B2", Method and System for calibrating a surgical tool and adaptor thereof—U.S. Pat. No. 7,166,114B2.

The disclosures of all publications and patent documents mentioned in the specification, and of the publications and patent documents cited therein directly or indirectly, are hereby incorporated by reference, other than subject matter disclaimers or disavowals. If the incorporated material is inconsistent with the express disclosure herein, the interpretation is that the express disclosure herein describes certain embodiments, whereas the incorporated material describes other embodiments. Definition/s within the incorporated material may be regarded as one possible definition for the term/s in question.

SUMMARY OF CERTAIN EMBODIMENTS

Certain embodiments of the present invention seek to provide circuitry typically comprising at least one processor in communication with at least one memory, with instructions stored in such memory executed by the processor to provide functionalities which are described herein in detail. Any functionality described herein may be firmware-implemented or processor-implemented as appropriate.

Certain embodiments seek to provide a computerized system aiding a surgeon end-user, the system comprising all or any subset of the following:
  a light projector typically configured to project at least one pattern onto at least one spine,
  plural 3d video cameras typically operative, when the spine is in their field of view, to capture typically 3d video imagery of the spine and pattern;
  a tool tracker aka tool adaptor; and
  a computer aka processor typically including logic configured to receive the output tool-status indication generated by the tool tracker and the 3d video imagery, and/or to track at least one vertebra of the spine, e.g. using the pattern, which may be known to the processor, and/or, accordingly to provide feedback (visual or otherwise) to the surgeon during the surgical procedure, thereby to provide direct tracking of vertebrae rather than of markers attached to the spine.

The tool tracker may include an inertial navigation subsystem (INS) to repeatedly compute an output tool-status indication of a current orientation aka angle aka angular orientation and of a current position of at least one tool aka surgical instrument used during a surgical procedure on the spine, thereby to provide inertial tracking of the tool's position and angle; and/or a wireless communication module operative to provide data communication between the subsystem and the processor including sending the output tool-status indication to the processor.

Any module, subsystem, apparatus, unit described herein may include a suitable logic or processor/s configured to perform the functionality described.

Certain embodiments are advantageous inter alia because feedback is provided within the surgeon's field of view while s/he performs the surgery and gazes at the surgical field.

Certain embodiments are advantageous inter alia because the position and/or angular orientations of tools and/or screws vis a vis a spine or other portion of the human body, are presented e.g. displayed to the surgeon end-user.

Certain embodiments seek to continuously determine each tool's position, e.g. by deriving, e.g. from marker tracking data, each tool's current 3d location and orientation.

Certain embodiments seek to provide a tool adaptor operable to assist surgeons in planning and performing spinal surgery.

Certain embodiments seek to provide a system and method which may be used in conjunction with conventional pre-operational planning including:
  taking a CT image of a patient's spine or portion thereof, and
  analysis of a CT image to determine which vertebrae will be operated on, and in what way, and
  generating a surgery plan.

The system may execute, or guide a surgeon to execute, all or any subset of the following operations:
Pre-op:
  Activation of CT scan analysis functionality which 'separates' the bone surfaces from the CT and provides a 3D model of the spine vertebrae.
  Activation of software which identifies, in the CT image, bone features most usable for tracking e.g. spinous process and lateral processes, e.g. as shown in FIG. 10.
As Surgery Begins:
  Display surgery plan to surgeon.
  Assuming surgeon mounts a tracker on each tool needed for that surgery, the system uses trackers mounted on tools, to give initial registration of each tool, e.g. responsive to surgeon's 'presenting' each tool in the camera's field of view. If tracking is lost for some reason, typically registration is repeated, and continuous tool tracking resumes.
  CT-to-3D image registration of vertebrae e.g. as shown and described herein, which may be performed only once per surgery.
  Typically, a digital CT scan or other image is received and the system generates output e.g. on a screen visible to the surgeon which separates bone from non-bone portions of the CT scan and/or displays each vertebrae separately as a 3D object.
  Extraction of bone features from pre-operational CT.
  It is appreciated that bone features to be tracked are, typically at this point, exposed by the surgeon.
Continuously, During Surgery, as Surgeon Goes Through her or his Surgery Plan:
  Tracking 3d position and orientation of each tool:
  Feedback to surgeon on position and orientation of surgery tool/s vs. pre-planning position and orientation;
  Real time tracking of vertebrae bone features—continuous individual vertebra-level tracking.

If tracking is lost for some reason, typically registration is repeated and continuous tracking resumes.

A bone removal app may be called up, which provides an ongoing estimate of the amount of bone removed, as well as the shape of the removed volume by comparing images of the vertebrae in sequential images thereof.

Planning for surgery typically requires accurate measurements of the human body, various clinical data, suggestions to the surgeon based on previous surgeries, and a simulation process. Use of computer aided surgical (CAS) systems that assist surgeons during surgery is quite known in the art. Such CAS systems are widely used during surgical procedures by surgeons for precise location and tracking of surgical instruments. Current CAS systems use preoperative images such as Magnetic Resonance Images (MRI) scans, and/or Computer Tomography (CT) scan images of a patient undergoing surgery without changes. However, when a patient moves during the surgery, due to breathing or manipulations done by the surgeon during the operation, the preoperative CT scan image may not serve as a good reference to use for precise location and tracking of surgical instruments.

Further, current CAS systems use markers for registration and calibration. The markers can be a plurality of optical emitters that can be detected by a navigation tool to determine position and orientation of a surgical instrument. However, existing CAS systems use of markers assume that distance between marker and relevant anatomy of a patient is fixed, however due to movements of the patient's body, the distance between the marker and relevant anatomy may change, thereby rendering calculations based on fixed markers inaccurate for tracking of surgical instruments.

Further, navigation tools deployed by current CAS systems fail to completely avoid occlusion caused during surgery due to the fingers, hand, head and arms, and other body parts of the surgeon. For example, if a body part of the surgeon interferes with the imaging, then tracking fails, and navigation stops. As a result, the operation may slow down or the operation may have to be performed in sub optimal or non-conducive positions. Furthermore, during surgery, current CAS systems fail to provide real-time and accurate feedback to the surgeon for reaching the desired anatomical portion during surgery.

Another challenge with present surgical navigation systems is the time required to properly apply and calibrate the tracking devices to work with conventional surgical instruments. For example, the following prior art is provided for supportive teachings, and is incorporated by reference.

Certain embodiments seek to provide a system and method for CAS, that provides real-time three-dimensional tracking of each vertebra of the spine during spinal surgeries, dynamic optimal markers for guiding navigation of surgical instruments, and real-time and accurate feedback to the surgeon for reaching the desired anatomical portion during surgery. Accordingly, an alternate system and method for assisting a surgeon in performing spinal surgeries is disclosed.

Certain embodiments seek to provide a method and system for assisting a surgeon in performing surgeries, especially of the spine. Certain embodiments seek to provide a real-time tracking of each vertebra of the spine that can compensate movement of the patient during surgery, and thereby provide accurate navigation feedback to a surgeon performing such surgery.

Certain embodiments seek to provide a system for providing assistance in surgery, the system comprising a scanner to track movement of each vertebra of a spine of a patient undergoing a surgery by capturing a three dimensional view of an anatomy and a surrounding scene of the patient; a surgery navigation tool including a tool adaptor comprising an inertial navigation system (INS) to track an angle and position of one or more surgical instruments used during the surgery; a camera fixed on the surgery navigation tool to enable the scanner to track the tool; and a projector to display an illuminated pattern of a relevant portion of the anatomy for visualization by the surgeon, and provide active feedback to the surgeon to aid navigation during the surgery based on signals received from a computing device and the surgery navigation tool.

Certain embodiments seek to provide a plurality of sensors within the scanner where each sensor has a distinct field of view (FOV) to track a set of optical markers placed within the FOV.

Certain embodiments seek to provide a 3D location and angle in space for the surgery navigation tool, and track the set of optical markers.

Certain embodiments seek to provide an active screen within the tool adaptor to direct the surgeon along a trajectory and position using a combination of arrows, wherein the arrows are illuminated to direct changes, and a display device within the tool adaptor to provide visual feedback regarding accuracy of the surgery.

Certain embodiments seek to provide the INS (inertial navigation system) based on gyroscopes, accelerometers, magnetometers, thermal sensors and other sensors and mechanisms to perform tracking of the angle and position.

Certain embodiments seek to provide a communication module to transfer data from the scanner and the computing device.

Certain embodiments seek to provide a processor and a memory storing computer readable instructions, which, when executed by the processor perform measuring predefined clinical parameters of the spine and the vertebrae; storing the clinical parameters in a database; storing a plurality of scans and three dimensional views of the relevant anatomy of the patient in the database; creating a registration between a two dimensional image in a standing posture and a three dimensional image in a standing posture, to enable the surgeon to correct the spine in the standing posture and determine a surgery plan; retrieving clinical cases with a surgery outcome of similar clinical parameters from the database for providing additional clinical support to the surgeon in determining the surgery plan, communicating the registration of the spine to the projector for display, and communicating a 3D reconstruction of the spine and the plurality of vertebras to a 3D printing manufacturing device.

Certain embodiments seek to provide a method for tracking, by a scanner, a movement of each vertebra of a spine of a patient undergoing surgery by capturing a three dimensional view of an anatomy and a surrounding scene of the patient; tracking, by an inertial navigation system (INS) inbuilt within a tool adaptor, an angle and position of one or more surgical instruments used during the surgery, wherein the tool adaptor is provided within a surgery navigation tool; directing, by an active screen coupled to the tool adaptor, using a combination of arrows, a navigation of the surgery navigation tool along a trajectory during the surgery, wherein the arrows are illuminated to direct changes in the navigation; tracking, by a camera fixed on the surgery navigation tool, to track the navigation of the surgery navigation tool; displaying, by a projector, an illuminated pattern of a relevant portion of the anatomy for visualization by the surgeon; and providing, by the projector, active feedback to the surgeon to aid navigation during surgery based on signals received from a computing device and the surgery navigation tool.

Certain embodiments seek to provide a plurality of sensors, each sensor having a distinct field of view (FOV) to track a set of optical markers placed within the FOV.

Certain embodiments seek to create, by the scanner, a 3D location and angle in space for the surgery navigation tool; and track by the scanner, the set of optical markers.

Certain embodiments seek to provide by a display device, a visual feedback regarding an accuracy of the surgery, wherein the display device is coupled to the tool adaptor.

Certain embodiments seek to provide a system method and computer program product for providing assistance to a surgeon during a spinal surgery. The system includes a scanner to track movement of each vertebra of a spine of a patient undergoing a surgery by capturing a three dimensional view of an anatomy and a surrounding scene of the patient, a surgery navigation tool including a tool adaptor 201 comprising an inertial navigation system (INS) to track an angle and position of one or more surgical instruments used during the surgery, a camera fixed on the surgery navigation tool to enable the scanner to track the tool, and a projector to display an illuminated pattern of a relevant portion of the anatomy for visualization by the surgeon, and provide active feedback to the surgeon to aid navigation during surgery based on signals received from a computing device and the surgery navigation tool.

The present invention typically includes at least the following embodiments:

Embodiment 1. A computerized system aiding a surgeon end-user, the system comprising:
  a light projector configured to project at least one pattern onto at least one spine, plural 3D video cameras operative, when the spine is in their field of view, to capture 3D video imagery of the spine and pattern;
  a tool tracker aka tool adaptor; and
  a computer aka processor including logic configured to receive the output tool-status indication generated by the tool tracker and the 3D video imagery, and to track at least one vertebra of the spine, using the pattern, which is known to the processor, and accordingly to provide feedback to the surgeon during a surgical procedure, thereby to provide direct tracking of vertebrae rather than of markers attached to the spine,
  the tool tracker comprising:
    an inertial navigation subsystem (INS) to repeatedly compute an output tool-status indication of a current orientation aka angle aka angular orientation and of a current position of at least one tool aka surgical instrument used during a surgical procedure on the spine, thereby to provide inertial tracking of the tool's position and angle; and
    a wireless communication module operative to provide data communication between the subsystem and the processor including sending the output tool-status indication to the processor.

Embodiment 2. A system according to any of the preceding embodiments wherein the feedback includes an indication, in at least near real time, of a current relative position and angle of the at least one tool relative to at least a portion of the spine.

Embodiment 3. A system according to any of the preceding embodiments wherein the feedback comprises visual feedback presented to the surgeon end-user on a display screen which is in data communication with the logic.

Embodiment 4. A system according to any of the preceding embodiments wherein the tool tracker is mounted on the tool.

Embodiment 5. A system according to any of the preceding embodiments wherein plural tool trackers are provided and are mounted on plural tools, thereby to enable plural tools to be tracked simultaneously.

Embodiment 6. A system according to any of the preceding embodiments wherein markers, used for tracking the tool, are fixed to the tool and/or tool tracker.

Embodiment 7. A system according to any of the preceding embodiments and also comprising a user interface via on which the surgeon end-user can mark at least one bone feature to be tracked, on the spine, and wherein the bone feature so marked is used to track at least a portion of the spine.

Embodiment 8. A system according to any of the preceding embodiments wherein the processor has access to digitally stored a priori knowledge of vertebrae shapes and of geometric relationships between adjacent vertebrae and wherein the processor is configured to segment the spine into individual vertebrae thereby to facilitate tracking of each individual vertebra of the spine.

Embodiment 9. A system according to any of the preceding embodiments wherein the tool tracker presents, to the surgeon end-user, visual feedback, generated by the processor, and sent to the tool tracker via the communication module, indicating how to change the tool's current angular orientation, including feedback including at least one of the tool's position, angular orientation and depth, thereby to provide the feedback to the surgeon end-user, without requiring the surgeon end-user to look away from the surgical field to view a screen distant from the surgical field.

Embodiment 10. A system according to any of the preceding embodiments wherein at least one LED is mounted on the tool tracker and wherein the at least one LED is controlled to provide the visual feedback.

Embodiment 11. A system according to any of the preceding embodiments wherein the a priori knowledge comprises at least one 3D model of at least one individual vertebra.

Embodiment 12. A system according to any of the preceding embodiments wherein the markers comprise fiducial markers.

Embodiment 13. A system according to any of the preceding embodiments wherein the markers comprise ball markers.

Embodiment 14. A system according to any of the preceding embodiments wherein the inertial navigation subsystem (INS) is operative to continually compute output tool-status indications of current angular orientations and current positions of the at least one tool.

Embodiment 15. A system according to any of the preceding embodiments wherein the projector projects the pattern using light beyond the visible spectrum.

Embodiment 16. A computer program product, comprising a non-transitory tangible computer readable medium having computer readable program code embodied therein, the computer readable program code adapted to be executed to implement a method comprising the following operations: Providing a light projector configured to project at least one pattern onto at least one spine, Providing plural 3D video cameras operative, when the spine is in their field of view, to capture 3D video imagery of the spine and pattern; Providing a tool tracker aka tool adaptor, the tool tracker comprising: an inertial navigation subsystem (INS) constructed and operative to repeatedly compute an output tool-status indication of a current orientation aka angle aka angular orientation and of a current position of at least one tool aka surgical instrument used during a surgical procedure on the spine, thereby to provide inertial tracking of the tool's position and angle; and a wireless communication module operative to provide data communication between the subsystem and a processor including sending the output tool-status indication to the processor; wherein the processor includes logic configured to receive the output tool-status indication generated by the tool tracker and the 3D video imagery, and to track at least one vertebra of the spine, using the pattern, which is known to the processor, and accordingly to provide feedback to the surgeon during a surgical procedure, thereby to provide direct tracking of vertebrae rather than of markers attached to the spine.

Embodiment 17. A computerized method aiding a surgeon end-user, the method comprising: Providing a light projector configured to project at least one pattern onto at least one spine, Providing plural 3D video cameras operative, when the spine is in their field of view, to capture 3D video imagery of the spine and pattern; Providing a tool tracker aka tool adaptor, the tool tracker comprising: an inertial navigation subsystem (INS) constructed and operative to repeatedly compute an output tool-status indication of a current orientation aka angle aka angular orientation and of a current position of at least one tool aka surgical instrument used during a surgical procedure on the spine, thereby to provide inertial tracking of the tool's position and angle; and a wireless communication module operative to provide data communication between the subsystem and a processor including sending the output tool-status indication to the processor; wherein the processor includes logic configured to receive the output tool-status indication generated by the tool tracker and the 3D video imagery, and to track at least one vertebra of the spine, using the pattern, which is known to the processor, and accordingly to provide feedback to the surgeon during a surgical procedure, thereby to provide direct tracking of vertebrae rather than of markers attached to the spine.

Embodiments also include:

Embodiment 101. A system, method or computer program product for providing assistance in surgery, comprising all or any subset of the following:
 a scanner to track movement of each vertebra of a spine of a patient undergoing surgery by capturing a three dimensional view of an anatomy and a surrounding scene of the patient;
 a surgery navigation tool including a tool adaptor 201 comprising an inertial navigation system (INS) to track an angle and position of one or more surgical instruments used during the surgery;
 a camera fixed on the surgery navigation tool to enable the scanner to track the tool; and
 a projector to:
  display an illuminated pattern of a relevant portion of the anatomy for visualization by the surgeon; and/or
  provide active feedback to the surgeon to aid navigation during the surgery based on signals received from a computing device and the surgery navigation tool.

Embodiment 102. The system of Embodiment 101, wherein the scanner further comprises:
 a plurality of sensors, each sensor having a distinct field of view (FOV) to track a set of optical markers placed within the FOV.

Embodiment 103. The system method or computer program product of any preceding embodiment wherein the scanner is a three dimensional (3D) scanner further configured to:
 create a 3D location and angle in space for the surgery navigation tool; and
 track the set of optical markers.

Embodiment 104. The system method or computer program product of any preceding embodiment wherein the tool adaptor 201 comprises:
 an active screen to direct the surgeon along a trajectory and position using a combination of arrows, wherein the arrows are illuminated to direct changes; and
 a display device to provide visual feedback regarding accuracy of the surgery.

Embodiment 105. The system of any preceding embodiment wherein the anatomy is the spine, wherein the spine comprises a plurality of vertebrae.

Embodiment 106. The system method or computer program product of any preceding embodiment wherein the INS of the tool adaptor 201 is based on gyroscope, accelerometers, magnetometers, thermal sensors and other sensors and mechanisms to perform tracking of the angle and position.

Embodiment 107. The system method or computer program product of any preceding embodiment, wherein the surgery navigation tool further comprises:
 a communication module to transfer data from the scanner and the computing device.

Embodiment 108. The system method or computer program product of any preceding embodiment wherein the computing device comprises:
 a processor; and
 a memory storing computer readable instructions which when executed by the processor performs:
  measuring pre-defined clinical parameters of the spine and the vertebrae;
  storing the clinical parameters in a database;
  storing a plurality of scans and three dimensional views of the relevant anatomy of the patient in the database;
  creating a registration between a two dimensional image in a standing posture, and a three dimensional image in a standing posture, to enable the surgeon to correct the spine in the standing posture and determine a surgery plan; and
  retrieving clinical cases with a surgery outcome of similar clinical parameters from the database for providing additional clinical support to the surgeon in determining the surgery plan.

Embodiment 109. The system method or computer program product of any preceding embodiment wherein the computing device is further configured to: communicate the registration of the spine to the projector for display.

Embodiment 110. The system method or computer program product of any preceding embodiment wherein the computing device is further configured to communicate a 3D reconstruction of the spine and the plurality of vertebras to a 3D printing manufacturing device.

The term process is intended to include medical terms describing bony projections off the posterior (back) part of spine vertebrae e.g. SP or Spinous Process, SAP or Superior Articular Process, IAP or Inferior Articular Process, etc.

It is appreciated that any reference herein to, or recitation of, an operation being performed is, e.g. if the operation is performed at least partly in software, intended to include both an embodiment where the operation is performed in its entirety by a server A, and also to include any type of "outsourcing" or "cloud" embodiments in which the operation, or portions thereof, is or are performed by a remote processor P (or several such), which may be deployed off-shore, or "on a cloud", and an output of the operation is then communicated to, e.g. over a suitable computer network, and used by, server A. Analogously, the remote processor P may not, itself, perform all of the operations and, instead, the remote processor P itself may receive output/s of portion/s of the operations from yet another processor/s P', may be deployed off-shore relative to P, or "on a cloud", and so forth.

Also provided, excluding signals, is a computer program comprising computer program code means for performing any of the methods shown and described herein when the program is run on at least one computer; and a computer program product, comprising a typically non-transitory computer-usable or -readable medium e.g. non-transitory computer-usable or -readable storage medium, typically tangible, having a computer readable program code embodied therein, the computer readable program code adapted to be executed to implement any or all of the methods shown and described herein. The operations in accordance with the teachings herein may be performed by at least one computer specially constructed for the desired purposes or general purpose computer specially configured for the desired purpose by at least one computer program stored in a typically non-transitory computer readable storage medium. The term "non-transitory" is used herein to exclude transitory, propagating signals or waves, but to otherwise include any volatile or non-volatile computer memory technology suitable to the application.

Any suitable processor/s, display and input means may be used to process, display e.g. on a computer screen or other computer output device, store, and accept information such as information used by or generated by any of the methods and apparatus shown and described herein; the above processor/s, display and input means including computer programs, in accordance with all or any subset of the embodiments of the present invention. Any or all functionalities of the invention shown and described herein, such as but not limited to operations within flowcharts, may be performed by any one or more of: at least one conventional personal computer processor, workstation or other programmable device or computer or electronic computing device or processor, either general-purpose or specifically constructed, used for processing; a computer display screen and/or printer and/or speaker for displaying; machine-readable memory such as flash drives, optical disks, CDROMs, DVDs, BluRays, magnetic-optical discs or other discs; RAMs, ROMs, EPROMs, EEPROMs, magnetic or optical or other cards, for storing, and keyboard or mouse for accepting. Modules illustrated and described herein may include any one or combination or plurality of: a server, a data processor, a memory/computer storage, a communication interface (wireless (e.g. BLE) or wired (e.g. USB)), or a computer program stored in memory/computer storage.

The term "process" as used above is intended to include any type of computation or manipulation or transformation of data represented as physical, e.g. electronic, phenomena which may occur or reside e.g. within registers and/or memories of at least one computer or processor. Use of nouns in singular form is not intended to be limiting; thus the term processor is intended to include a plurality of processing units which may be distributed or remote, and the term server is intended to include plural, typically interconnected modules, running on plural respective servers, and so forth.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements all or any subset of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may, wherever suitable, operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless stated otherwise, terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining", "providing", "accessing", "setting" or the like, refer to the action and/or processes of at least one computer/s or computing system/s, or processor/s or similar electronic computing device/s or circuitry, that manipulate and/or transform data which may be represented as physical, such as electronic, quantities e.g. within the computing system's registers and/or memories, and/or may be provided on-the-fly, into other data which may be similarly represented as physical quantities within the computing system's memories, registers or other such information storage, transmission or display devices, or may be provided to external factors e.g. via a suitable data network. The term "computer" should be broadly construed to cover any kind of electronic device with data processing capabilities, including, by way of non-limiting example, personal computers, servers, embedded cores, computing system, communication devices, processors (e.g. digital signal processor (DSP), microcontrollers, field programmable gate array (FPGA), application specific integrated circuit (ASIC), etc.) and other electronic computing devices. Any reference to a computer, controller or processor is intended to include one or more hardware devices e.g. chips, which may be co-located or remote from one another. Any controller or processor may for example comprise at least one CPU, DSP, FPGA or ASIC, suitably configured in accordance with the logic and functionalities described herein.

Any feature or logic or functionality described herein may be implemented by processor/s or controller/s configured as per the described feature or logic or functionality, even if the processor/s or controller/s are not specifically illustrated for simplicity. The controller or processor may be implemented in hardware, e.g., using one or more Application-Specific Integrated Circuits (ASICs) or Field-Programmable Gate Arrays (FPGAs), or may comprise a microprocessor that runs suitable software, or a combination of hardware and software elements.

The present invention may be described, merely for clarity, in terms of terminology specific to, or references to, particular programming languages, operating systems, browsers, system versions, individual products, protocols and the like. It will be appreciated that this terminology or such reference/s is intended to convey general principles of operation clearly and briefly, by way of example, and is not intended to limit the scope of the invention solely to a particular programming language, operating system, browser, system version, or individual product or protocol. Nonetheless, the disclosure of the standard or other professional literature defining the programming language, operating system, browser, system version, or individual product or protocol in question, is incorporated by reference herein in its entirety.

Elements separately listed herein need not be distinct components and alternatively may be the same structure. A statement that an element or feature may exist is intended to include (a) embodiments in which the element or feature exists; (b) embodiments in which the element or feature does not exist; and (c) embodiments in which the element or feature exist selectably e.g. a user may configure or select whether the element or feature does or does not exist.

Any suitable input device, such as but not limited to a sensor, may be used to generate or otherwise provide information received by the apparatus and methods shown and described herein. Any suitable output device or display may be used to display or output information generated by the apparatus and methods shown and described herein. Any suitable processor/s may be employed to compute or generate information as described herein and/or to perform functionalities described herein and/or to implement any engine, interface or other system illustrated or described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

The system shown and described herein may include user interface/s e.g. as described herein which may for example include all or any subset of: an interactive voice response interface, automated response tool, speech-to-text transcription system, automated digital or electronic interface having interactive visual components, web portal, visual interface loaded as web page/s or screen/s from server/s via communication network/s to a web browser or other application downloaded onto a user's device, automated speech-to-text conversion tool, including a front-end interface portion thereof and back-end logic interacting therewith. Thus the term user interface or "ui" as used herein includes also the underlying logic which controls the data presented to the user e.g. by the system display and receives and processes and/or provides to other modules herein, data entered by a user e.g. using her or his workstation/device.

BRIEF DESCRIPTION OF THE DRAWINGS

Example embodiments are illustrated in the various drawings. The accompanying drawings illustrate various embodiments of systems, methods, and embodiments of various other aspects of the disclosure. Any person with ordinary skill in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale. Specifically:

FIGS. 8a, 8b, 9a-9c are visual presentations of individual vertebrae which may be generated by the GUI shown and described herein.

Figure 1:
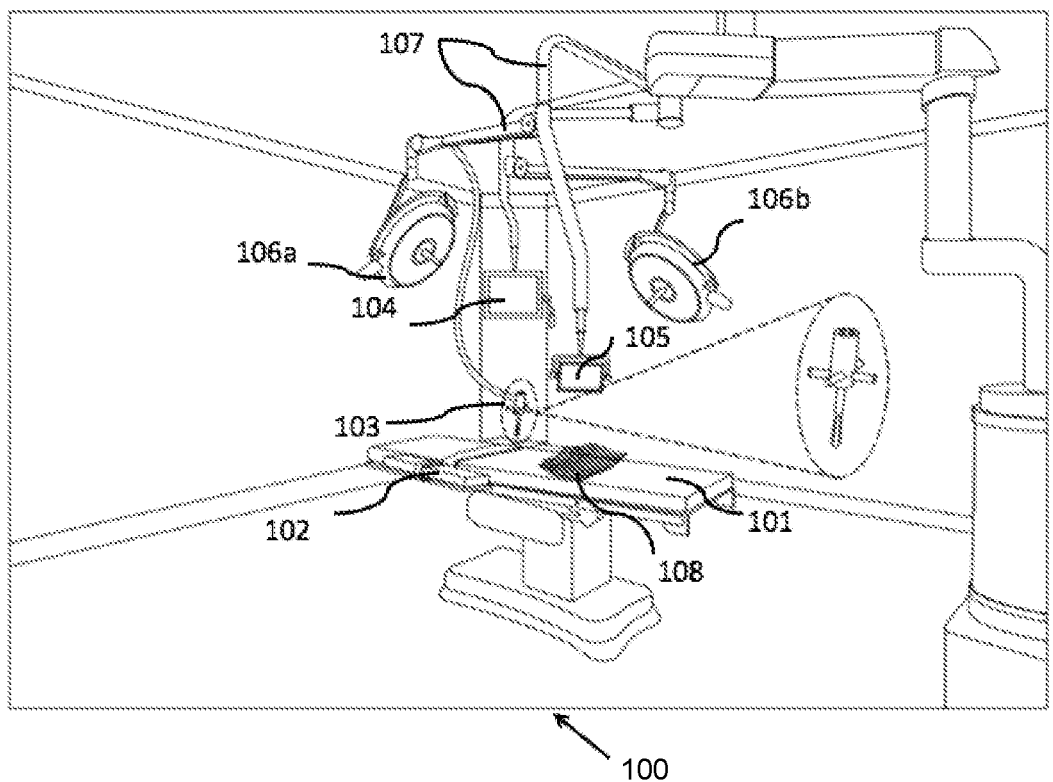
FIG. 1 illustrates an environment 100 including a system that provides assistance to a surgeon during a spinal surgery, according to an embodiment.

Certain embodiments of the present invention are illustrated in the following drawings; in the block diagrams, arrows between modules may be implemented as APIs and any suitable technology may be used for interconnecting functional components or modules illustrated herein in a suitable sequence or order e.g. via a suitable API/Interface. For example, state of the art tools may be employed, such as but not limited to Apache Thrift and Avro which provide remote call support. Or, a standard communication protocol may be employed, such as but not limited to HTTP or MQTT, and may be combined with a standard data format, such as but not limited to JSON or XML.

Methods and systems included in the scope of the present invention may include any subset or all of the functional blocks shown in the specifically illustrated implementations by way of example, in any suitable order e.g. as shown. Flows may include all or any subset of the illustrated operations, suitably ordered e.g. as shown. Tables herein may include all or any subset of the fields and/or records and/or cells and/or rows and/or columns described.

In the swim-lane diagrams, it is appreciated that any order of the operations shown may be employed rather than the order shown, however, preferably, the order is such as to allow utilization of results of certain operations by other operations by performing the former before the latter, as shown in the diagram.

Computational, functional or logical components described and illustrated herein can be implemented in various forms, for example, as hardware circuits such as but not limited to custom VLSI circuits or gate arrays or programmable hardware devices such as but not limited to FPGAs, or as software program code stored on at least one tangible or intangible computer readable medium and executable by at least one processor, or any suitable combination thereof. A specific functional component may be formed by one particular sequence of software code, or by a plurality of such, which collectively act or behave or act as described herein with reference to the functional component in question. For example, the component may be distributed over several code sequences such as but not limited to objects, procedures, functions, routines and programs and may originate from several computer files which typically operate synergistically.

Each functionality or method herein may be implemented in software (e.g. for execution on suitable processing hardware such as a microprocessor or digital signal processor), firmware, hardware (using any conventional hardware technology such as Integrated Circuit technology) or any combination thereof.

Functionality or operations stipulated as being software-implemented may alternatively be wholly or fully implemented by an equivalent hardware or firmware module and vice-versa. Firmware implementing functionality described herein, if provided, may be held in any suitable memory device and a suitable processing unit (aka processor) may be configured for executing firmware code. Alternatively, certain embodiments described herein may be implemented partly or exclusively in hardware in which case all or any subset of the variables, parameters, and computations described herein may be in hardware.

Any module or functionality described herein may comprise a suitably configured hardware component or circuitry. Alternatively or in addition, modules or functionality described herein may be performed by a general purpose computer or more generally by a suitable microprocessor, configured in accordance with methods shown and described herein, or any suitable subset, in any suitable order, of the operations included in such methods, or in accordance with methods known in the art.

Any logical functionality described herein may be implemented as a real time application, if, and as appropriate, and which may employ any suitable architectural option, such as but not limited to FPGA, ASIC or DSP or any suitable combination thereof.

Any hardware component mentioned herein may in fact include either one or more hardware devices e.g. chips, which may be co-located or remote from one another.

Any method described herein is intended to include within the scope of the embodiments of the present invention also any software or computer program performing all or any subset of the method's operations, including a mobile application, platform or operating system e.g. as stored in a medium, as well as combining the computer program with a hardware device to perform all or any subset of the operations of the method.

Data can be stored on one or more tangible or intangible computer readable media stored at one or more different locations, different network nodes or different storage devices at a single node or location.

It is appreciated that any computer data storage technology, including any type of storage or memory and any type of computer components and recording media that retain digital data used for computing for an interval of time, and any type of information retention technology, may be used to store the various data provided and employed herein. Suitable computer data storage or information retention apparatus may include apparatus which is primary, secondary, tertiary or off-line; which is of any type or level or amount or category of volatility, differentiation, mutability, accessibility, addressability, capacity, performance and energy use; and which is based on any suitable technologies such as semiconductor, magnetic, optical, paper and others.

DETAILED DESCRIPTION OF CERTAIN EMBODIMENTS

FIG. 1 illustrates an environment 100 of a computer aided surgery (CAS) system for providing assistance to a surgeon performing a surgery for the spine especially. The CAS system includes a monitor 104, a three dimensional (3D) scanner 105, mechanical linkage(s) 107, a surgical navigation tool 103, and surgical room lighting 106a-b. The environment 100 also includes a surgery table 102, on which a patient 101 is lying down with incisions on the back, and a stimulator 108 that stimulates the patient 101.

The 3D scanner 105 is used to track one or more surgical tools used during surgery and by calibration combine both systems to a single device. In certain embodiments of this invention, typically the 3D scanner 105 does both functions, and/or an additional function of scene analysis. The 3D scanner 105 is typically based on one or more of known 3D capturing methods and their variants. Light is typically projected in a known pattern where the pattern can be constant, Chroma dependent or time dependent. Another method that may be used is depth from defocus (or focus) whereby changing the focus depth and the location in space, e.g. either by mechanically moving one or more lenses, or using a liquid lens or any other type of lens with changing parameters. For example, the 3D scanner 105 can have following parameters: range of 1-2 meters, Field of View (FOV) of 400 mm×200 mm, 100×100 mm or 100 m×1000 m, resolution of 0.1 mm, minimum resolution of 0.5 mm minimum, accuracy of 0.3 mm, minimum accuracy of 1 mm, a Projection wavelength of 700-900 nm, Imaging wavelength of 400-900 nm, and a wireless communication capability.

A digital projector based on DLP, MEMS or any other method to project changing pattern may be used as part of the 3D scanner 105. In addition to such a use, a visible light based projection may be used as guidance to the surgeon. The digital projector can create an illuminated pattern, such as a spot or a circle or any pattern, on the relevant anatomy of the patient 101. For example, creating a circle on the pedicle area of the patient 101, where the surgeon is about to drill. An advantage of creating an illuminated pattern is that the surgeon can concentrate his/her view on the patient 101, rather than looking at a remote screen. As a result, the surgery can be completed faster, with greater accuracy. Further, creating an illumination on the correct part of the anatomy increases the trust of the surgeon, due to demonstrated ability of the system to recognize the anatomy and guide the surgeon.

In an embodiment, the 3D scanner 105 can also provide a scene and scene analysis viz. a 3D view of the surgery surrounding, and an anatomy of the patient 101. For example, in a robotic assisted surgery, the 3D scanner 105 can work in combination with a set of cameras that are installed on the robot itself to provide the robot with scene analysis.

In an embodiment, the 3D scanner 105 can have sensors with different FOV. One sensor can have high resolution to see the bones with high accuracy, and another sensor can be deployed to capture the scene in general. For example, relevant parameters for the 3D scanner can include a scanner height of 0.5-1.5 m from the surgery table 102, a FOV of 150-400 mm diameter for the high-resolution sensor, a pixel resolution of 0.1 mm when used with a 10 Megapixel camera, a FOV of 400-1000 mm for a low resolution sensor, and when used with 10 Mpixel camera the pixel resolution can reach up to 0.3 mm. Achieved pixel resolution by aforesaid 3D scanner 105 is higher than a state of art high-resolution CT scanner.

In an embodiment, the 3D scanner 105 can be connected to a ceiling or a wall of the surgery room by mechanical linkage(s) 107. The mechanical linkage(s) 107 can be a mechanical arm that can be used for 3D movement of the 3D scanner 105 with respect to the environment 100.

Further, the 3D scanner 105 can include a plurality of sensors to track movements of the surgeon and the surgical tools used during surgery of the patient 101. For example, the plurality of sensors can be used to track fixed items in the operating theatre, such as, but not limited to the operating table. Further, the 3D scanner 105 can track a plurality of predefined optical markers that are set in the FOV on a stable object such as a ceiling or a wall. Further, an additional sensor placed on top of the 3D scanner 105 can be oriented to view up towards the ceiling where the plurality of optical markers are set.

Furthermore, the 3D scanner 105 can track the movement of each vertebra of a spinal cord of the patient 102, in real-time that compensates for any movement by the patient 102. For example, movements can be due to breathing of the patient 102 or due to manipulations by the surgeon during the operation. The 3D scanner 105 can also support a robotic arm in robotic surgery. The 3D scanner 105 can guide the robotic arm in a 3D space and enable maneuvering around obstacles by receiving real time accurate feedback to reach an anatomical area.

The surgical navigation tool 103 overcomes occlusion caused in navigation.

Figure 2:
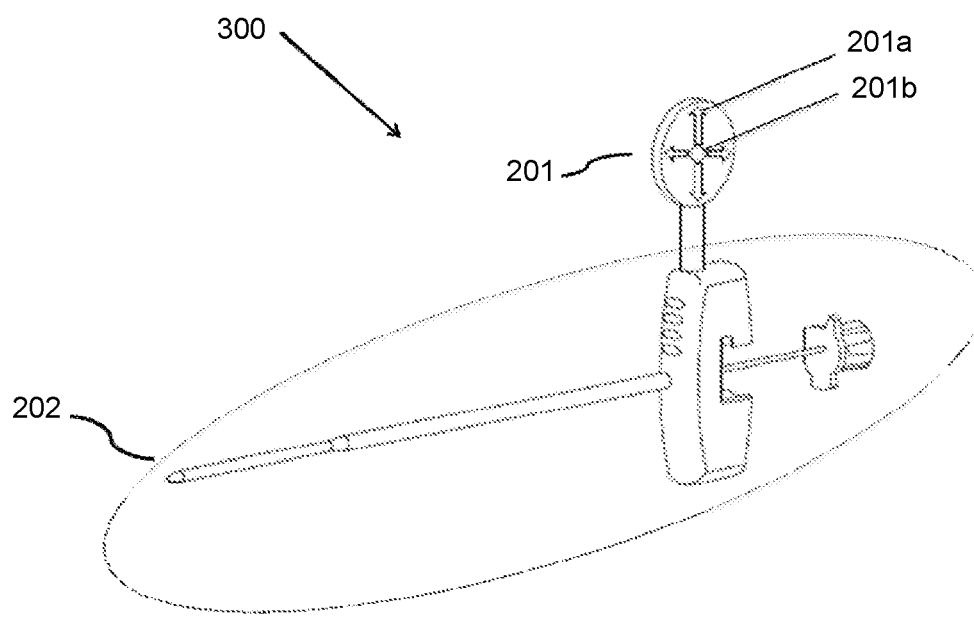
FIG. 2 depicts a surgical navigation tool 103 with a tool adaptor 201, according to an embodiment.

FIG. 2 depicts a surgical navigation tool 103 with a tool adaptor 201, according to an embodiment. Just one example is depicted in FIG. 2; other attachments or arrangements can be included such as an LED/LCD screen for viewing the surgery. The tool adaptor 201 has an intrinsic tracking capability. This is based on an Inertial Navigation System (INS) that is based on gyroscope, accelerometers, magnetometers, thermal sensors and other sensors and mechanisms, which perform the tracking of angle and position. Internal mechanisms are better as they are robust against occlusion, and, combined with external tracking, allow more accurate location. The result is easier to use and more accurate navigation and tool tracking. INS tracking works in conjunction with the 3D scanner 105, throughout most of the process. The combined tracking creates more accurate and robust tool tracking, compared to current state-of-the-art, which is based solely on 3D camera & wireless triangulation with passive or active transponders.

The tool adaptor 201 has also communication capabilities, to receive and transfer data from the computer and from the 3D scanner and support synchronization between all system parts.

In the present invention typically, the navigation system is based on feedback to the surgeon coming either from a computer screen, which presents both spine (or spine elements) and tools together—showing their position and angle relationship, or an augmented reality concept which presents a similar visual feedback superimposed on top of the physical world.

The present invention typically uses internal feedback mechanisms that can be added to both methods. The tool adaptor 201 has an active screen (not shown in FIG. 2) or illumination that can direct the surgeon to the right trajectory and position. It uses a combination of arrows—lit to direct the changes and a "traffic-light" LED 201*a* to feedback for the accuracy. The LED 201*a* light is green when the surgery navigation tool is on target, and when it is slightly away from the target it turns to yellow, and finally when it is too far away from the target then it turns to red color. Any other type of internal feedback is possible—for example a digital screen—that can guide the movement of the surgeon. The tool adaptor has also four navigation keys (represented as arrows, 201*b*), for navigating the surgery navigation tool to left, right, up, and down.

An active screen is an electronic screen (such as those found in smart watches) that is capable of presenting information, both graphic and textual, to the surgeon, in real-time.

The method of the present invention typically obviates the need to look at the screen in the final usage of the tool, and/or obviates the need to handle complicated augmented reality systems.

In another embodiment, involving minimally invasive surgery, where there are not enough bones to create real time 3D registration to the pre-operative surgery, a use of a miniature or endoscopic camera can be inserted into a small incision. Further, an image of bones inside the incision can be taken to create a registration of a CT scan. The camera can use the hollow part of the screw to see the insertion path. A camera of size smaller than 2 mm is ideal, but even a camera of 2-8 mm can be used.

Figure 3A:
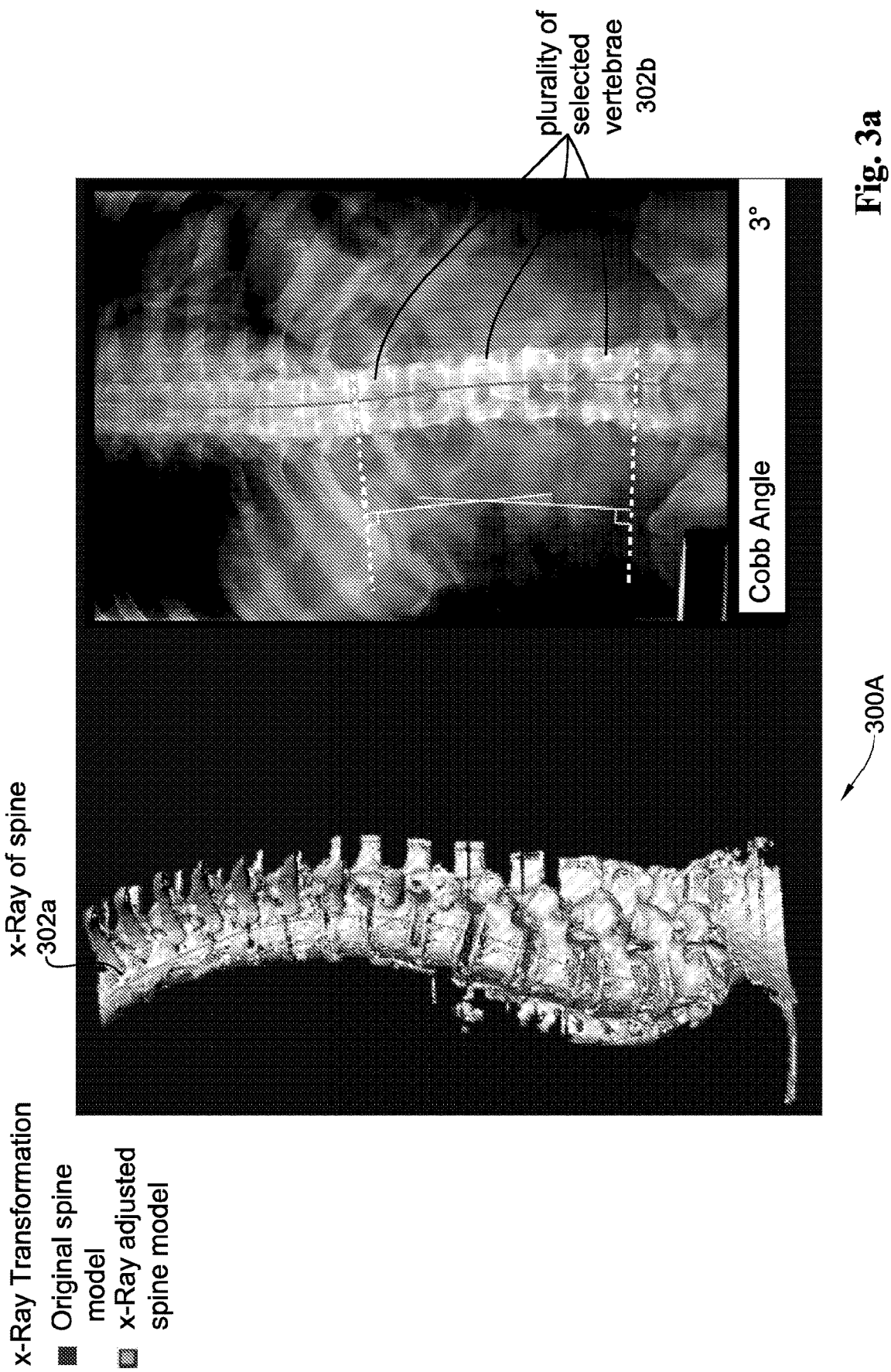
FIG. 3A is a graphical representation of registration created on selected vertebrae of the spine by surgery planning software, according to an embodiment.

Further, surgery planning software, running on a computer system, is deployed to automatically detect a spine in a CT scan and further vertebrae in the spine. By use of various computer vision and machine learning algorithms, detection is more accurate. Surgery planning software then presents the surgeon with a 3D and 2D reconstruction of the spine, which eliminates occlusion and supports better clinical evaluation of the patient. Typically, registration algorithms use extra information to improve a probability and quality of the registration. A CT scan used in surgery planning software undergoes a series of image enhancement algorithms such as noise reduction, smoothing, super resolution and feature detection, based on spine and vertebrae detection. Based on surgery planning, registration algorithms create a registration on the selected vertebrae as shown in FIG. 3A. The registration algorithms use extra information to improve the probability and quality of the registration. The CT scan used in the planning SW undergoes a series of image enhancement algorithms such as noise reduction, smoothing, super resolution and feature detection based on spine and vertebrae detection. Based on surgery planning, the registration algorithms try to create registration on the relevant vertebrae only: those vertebrae defined by the surgeon in the planning process. In case of change, the surgeon may use the computer to choose and define the relevant vertebrae for the surgery. The 3D scanner uses additional visual cues to create a smaller search area for the registration: for example, based on the patient's visible anatomy, the system estimates the location of the relevant vertebra in the back and starts the search there. Another cue is the location of the opening in the body.

FIG. 3A is a graphical representation 300A of a registration created on selected vertebrae of the spine by surgery planning software, according to an embodiment. A CT scan of a spine 302a is taken and the surgery planning software creates a registration, as shown, of a plurality of selected vertebrae 302b, as shown. The surgeon in the planning process defines the plurality of selected vertebrae 302b. In case of change, the surgeon may use the computer to choose and define the relevant vertebrae for the surgery. In an embodiment, the 3D scanner 105 can use additional visual cues to create a smaller search area for the registration. For example, based on the patient's visible anatomy, the 3D scanner 105 can estimate the location of the relevant vertebrae in the back and start the search there. Another cue is the location of the opening in the body.

Further, the surgery planning software measures pre-defined clinical parameters of the spine and vertebrae. These parameters are stored into a database for further analysis and presented to the surgeon for manual analysis. The surgery planning software can further perform analysis on the plurality of selected vertebrae 302b and illustrate detailed parameters of each selected vertebrae as shown in FIG. 3B.

Figure 3B:
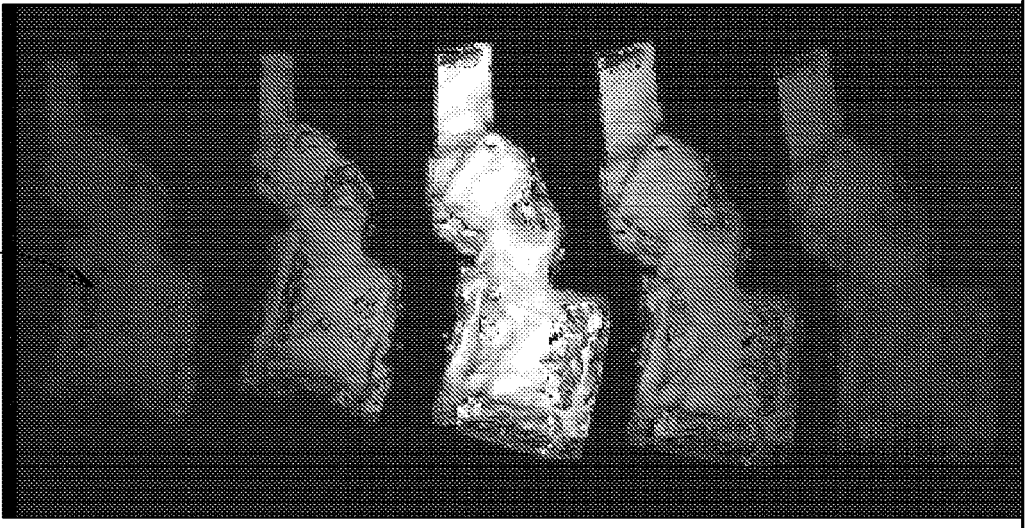
FIG. 3B shows graphical representation of the vertebral analysis of the selected vertebrae as created by the surgery planning software, and/or various vertebrae measurements, according to an embodiment.

FIG. 3B shows a graphical representation 300B of vertebrae analysis of the plurality of selected vertebrae 302b as created by the surgery planning software, according to an embodiment. A detailed information of a vertebra 308 can be shown on a right hand side of the graphical representation 300B. For example, detailed representation of vertebra L3 is shown in 308.

Figure 3C:
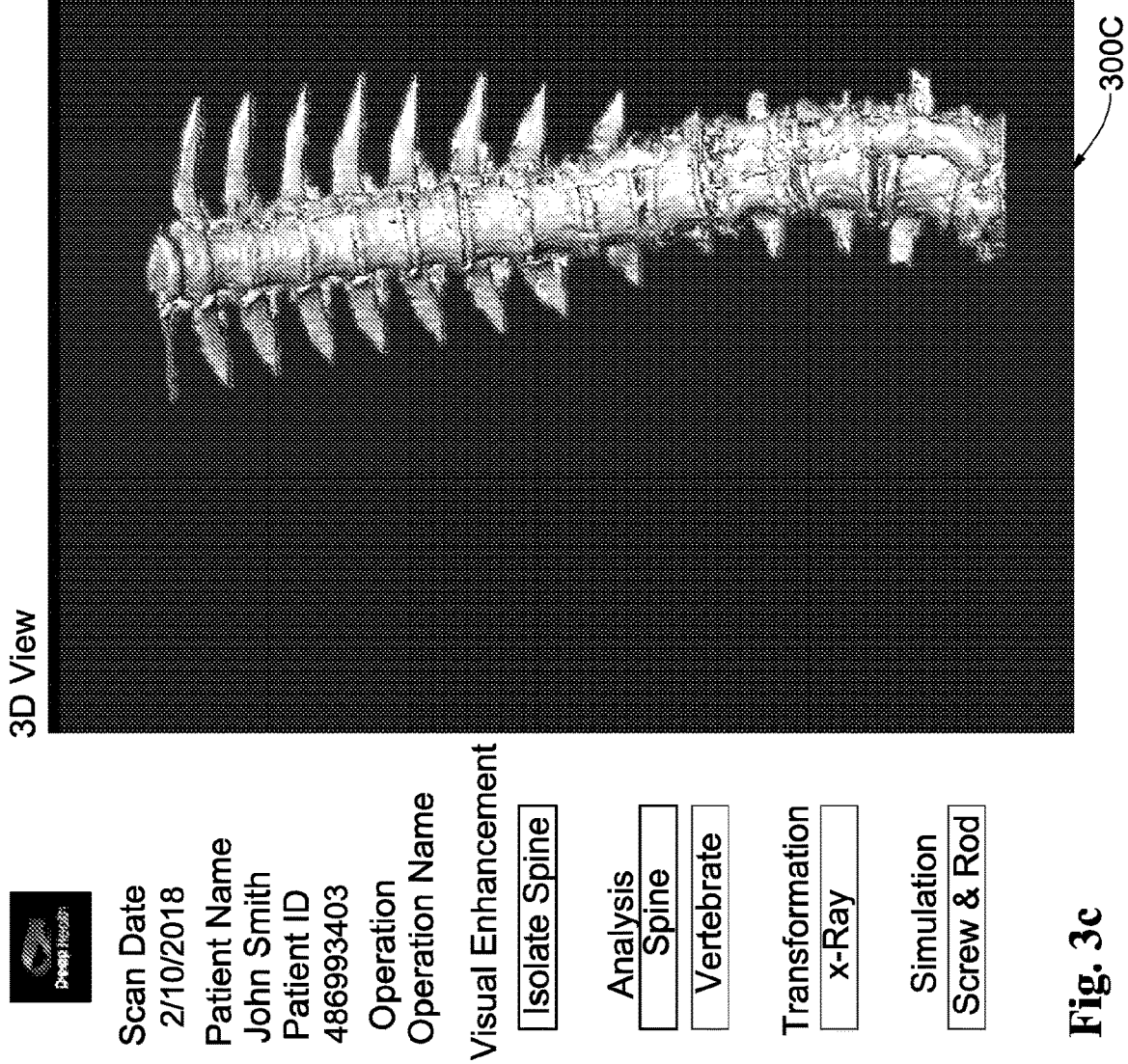
FIG. 3C shows a three dimensional representation of the spine, according to an embodiment.

Further, surgery planning software can create registration between a 2D X-ray taken in standing posture, and a 3D CT scan, which is taken in lying posture. The registration is done at the vertebra level. This results is in a visualization of the different spine curve in both postures, which enables the surgeon to correct the spine for a standing posture, instead of a lying down posture. FIG. 3C shows a three dimensional representation 300C of the spine, according to an embodiment. The 3D reconstruction of the spine 300C can be sent directly to a 3D printing or manufacturing device. This is done without additional input and manual manipulation by an external technician. The surgery plan can be used to define the exact implants to be used in the surgery and can allow ordering only specific implants. Further, production of custom-made implants and rods are made possible. Furthermore, production of custom-made surgery guides, as well as patient specific surgery tools and instruments, is made possible.

Further, the software presents the surgeon with 3D and 2D reconstruction of the spine, which eliminates occlusion and supports better clinical evaluation of the patient. The software measures pre-defined clinical parameters of the spine and vertebrae. The clinical parameters are stored into a database for further analysis and presented to the surgeon for manual analysis. For example: measuring a level of calcium in the bone can lead to an osteoporosis diagnosis which can affect the surgeon's decision-making and planning. When available, the software uses additional clinical data such as X-ray images in different positions (standing, bending, etc.), age, gender, height, weight, general clinical data of the patient and his/her health condition, as well as genetic information. By use of the database, similar cases can be found, and the surgeon can receive a clinical case with decisions made by another surgeon, and results of a previous surgery. Using aforesaid information, the surgeon may decide to alter a surgery plan.

Embodiments of surgery planning software may be provided as a computer program product, which may include a computer-readable medium tangibly embodying thereon, instructions, which may be used to program a computer (or other electronic devices) to perform a process. The computer-readable medium may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions (e.g., computer programming code, such as software or firmware). Moreover, embodiments of the present disclosure may also be downloaded as one or more computer program products, wherein the program may be transferred from a remote computer to a requesting computer by way of data signals embodied in a carrier wave or other propagation medium via a communication link (e.g., a modem or network connection).

Figure 4:
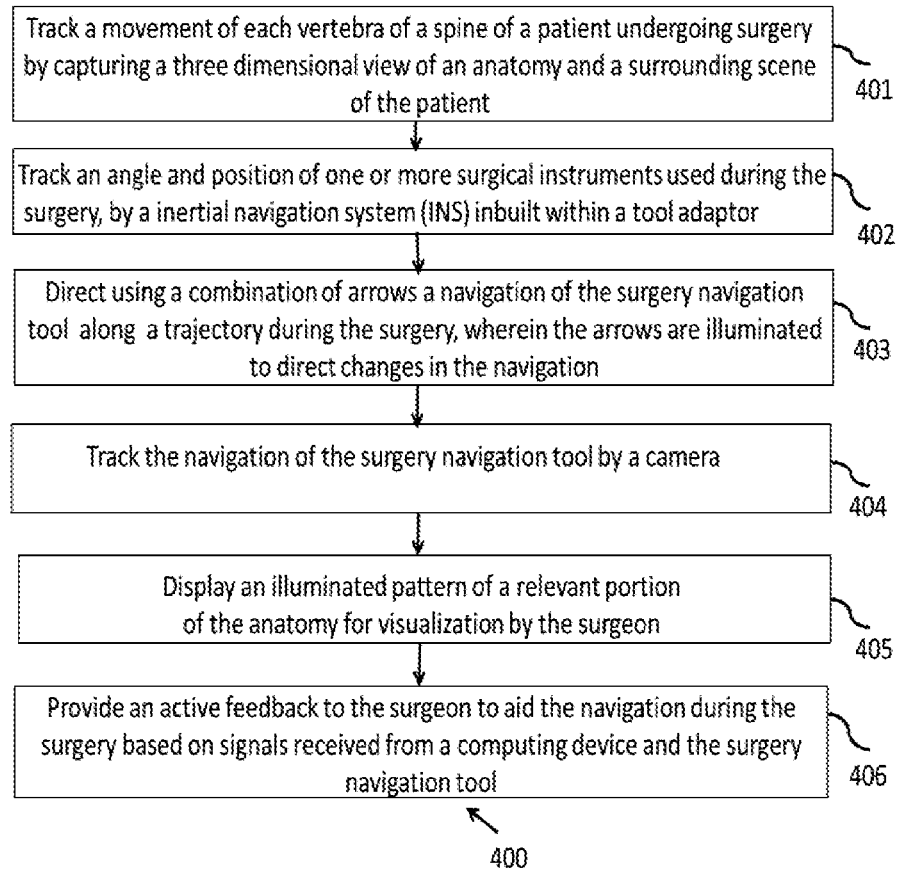
FIG. 4 illustrates a flowchart 400 showing a method for providing computer-aided assistance to a surgeon performing a spinal surgery.

The flowchart 400 of FIG. 4 shows a method for providing assistance to a surgeon during a spinal surgery. Each block may represent a module, segment, or portion of code, which comprises one or more executable instructions for implementing the specified logical function(s). It should also be noted that in some alternative implementations, the functions noted in the blocks may occur out of the order noted in the drawings, or not at all. For example, two blocks shown in succession in FIG. 4 may in fact be executed substantially concurrently, or the blocks may sometimes be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of the order from that shown or discussed, including substantially concurrently, or in reverse order, depending on the functionality involved. In addition, the process descriptions or blocks in flow charts should be understood as representing decisions made by a hardware structure such as a state machine. The flowchart 400 starts at the step 401 and proceeds to step 406.

At step 401, a movement of each vertebra of a spine of a patient undergoing surgery can be tracked by a scanner, by capturing a three dimensional view of an anatomy and a surrounding scene of the patient.

At step 402, an angle and position of one or more surgical instruments used during the surgery, is tracked by a inertial navigation system (INS) inbuilt within a tool adaptor of a surgical navigation tool.

At step 403, using a combination of arrows, a navigation of the surgery navigation tool is directed along a trajectory during the surgery, wherein the arrows are illuminated to direct changes in the navigation.

At step 404, the navigation of the surgery navigation tool is tracked by a camera affixed on top of the surgical navigation tool.

At step 405, an illuminated pattern of a relevant portion of the anatomy for visualization by the surgeon is displayed on a projector, to enable the surgeon to view the highlighted portion. For example, a circle on a pedicle area can be created so that the surgeon can focus his/her view on the patient, instead of looking at a remote screen.

At step 406, an active feedback is provided to the surgeon to aid navigation during surgery based on signals received from a computing device and the surgery navigation tool. The signals from the computing device may include results of past surgeries, registration of X-Ray to CT scans, and 3D reconstruction of the spine of the patient. The signals from the navigation tool include angle and position in space of the tool based on real-time tracking by the scanner and the images taken by the camera affixed on top of the surgical navigation tool.

The hardware components of the system shown and described herein typically include all or any subset of:
  i. Near InfraRed (NIR) 3d video imaging subsystem 1100 in FIG. 5 that images the spine vertebrae and surgery tools, for tracking by the software (iii below).
  ii. Tool tracker that includes all or any subset of the following internal components: Inertial Measurement Unit (IMU) chip including accelerometers and gyros, wireless communication module, indicator LEDs or screen for user feedback, fiducial/ball markers for tool tracking, battery.
  The tool tracker may be mounted on legacy tools or tools may be provided which include an integrally formed tracker, typically adjacent the tool's back end, e.g. as far as possible from the tool's tip.
  iii. Computer e.g. PC that runs the software functionalities shown and described herein and connects to both the 3D camera and Tool trackers by either wired or wireless communications.
  The computer may, if desired, be integrated with the camera.
  iv. Display screen providing displays representing outputs generated by various applications and functionalities described herein.

Figure 5:
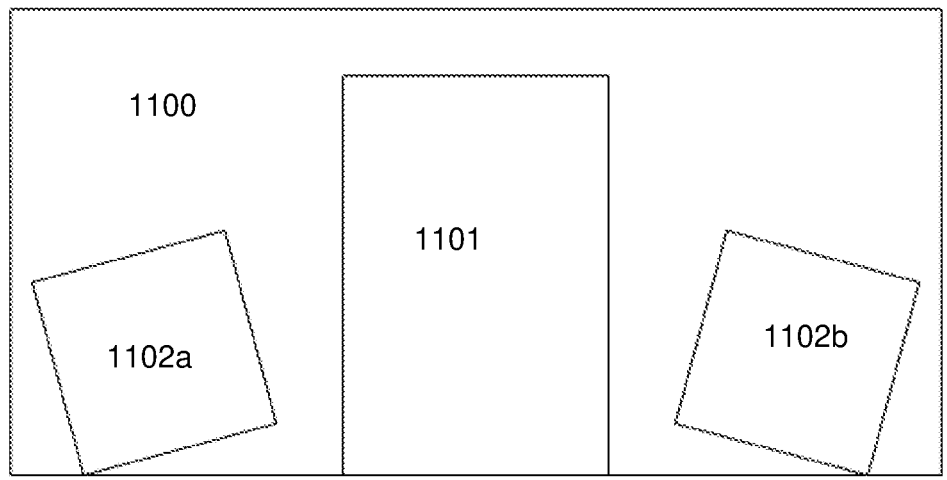
FIG. 5 is a simplified diagram of a camera system.

The design and specifications of the NIR 3D video imaging sub system 1100 aka 3D camera system is typically uniquely optimized for spine surgery. As shown in FIG. 5, the NIR 3D video imaging subsystem 1100 typically includes:
  a. A structured NIR light projector 1101 such as, say, the Shenzen Anhua Optoelectronics Technology model M8M-NIR, or any other suitable Near infrared aka NIR structured light projection module for 3D measurement which can be deployed or positioned by the surgeon to illuminate the surgical field; and
  b. A plurality of conventional 3D video cameras 1102*a* and 1102*b* such as, say, Hikvision MV-CE013-80UM Monochrome 1/2.7" 4□7 m CMOS USB3.0 1280×1024@148 fps cameras with MVL-MF1620M-5MP f=16 mm, F #2.0, 2/3", 5MP lenses. Typically, to ensure 3D depth reconstruction at sub-millimeter accuracy at least two cameras are provided; additional cameras typically provide even better accuracy at the cost of increased system complexity and cost.

The projector 1101 and cameras 1102 of the NIR 3D video imaging subsystem 1100 are all typically integrated in a single housing, where the cameras 1102 are placed on both sides of projector 1101. The exact position of the cameras 1102 vs. the projector 1101 may be calibrated and maintained during system assembly to ensure accurate depth measurement by the system. For an expected pixel accuracy of 0.3 mm, the distances between the cameras 1102 and projector 1101 are typically maintained within 0.1 mm or less of the distance measured during calibration. The system may undergo periodic testing on known targets to ensure calibration accuracy.

The structured light projector 1101 typically projects NIR (for example, 850 nm wavelength) light forming a pattern, known to the software, that illuminates the target. The pattern may be a random dot pattern, lines, binary coded images, or any other patterns known in the art.

The 3D image processing software is typically operative to:
  i. receive video streams showing identical illumination patterns imaged by the plural cameras,
  ii. determine the pixel offsets between simultaneous images from plural cameras, and then
  iii. determine each image pixel's distance from the camera subsystem 1100 as a function of the pixel offsets.

Every pixel in the image typically has X, Y, Z (depth) coordinates. Each tool and each vertebra position is typically continuously tracked by the system e.g. by knowing the tool or vertebra's last position and the tracked features to determine its new position. For tools—the tracked feature used to determine a tool's new position may include specific tool markers such as fiducials, balls, etc. For vertebrae—the tracked feature used to determine a new position may include specific bone features determined by the surgeon e.g. as described herein.

Software functionality may be used in the system to provide 3D pixel data from the camera images. For example, the opensourceimaging.org/project/structured-light-3d-scanner/website is an example project using (open source) software to yield a 3D scanner system from a commercial visible light projector (e.g. InFocus LP330), two off-the-shelf webcams (e.g. Logitech C920C) and Python code based on OpenCV and NumPy packages.

Use of NIR light ensures that the pattern, which is not seen by the surgeon, does not interfere with the surgery. The illumination wavelength is typically chosen to coincide with the wavelength at which the cameras are maximally responsive, thereby providing maximum image contrast.

The baseline distance between the cameras 1102 and the field of view of projector 1101 are typically selected by the camera designer, to match the required field of view and distance from the patient for optimal performance in spine surgery. For example, perhaps the field of view needs to be larger than about 400 mm×200 mm to cover the relevant area (on which surgery is to be performed) along the spine and areas adjacent this relevant area. The distance from the camera to the "target", aka patient's back or spine, may be between 1200 mm to 1500 mm to ensure the camera does not interfere with the surgery, yet tracks different tools that the surgeon may use during surgery. The resolutions of both scanner and cameras is typically equal, to produce pixels small enough, e.g. smaller than 0.33 mm at the surgery site or field, or any other value which is enough to provide accurate registration and tracking of the spine and tools.

The desired margin of error for placing a pedicle screw in a spine vertebrae may be 1 mm or less. A typical pedicle screw diameter is 4.5 mm to 7.5 mm (for example, pedicle screw set offered by VTI, e.g. at vti-spine.com/product/interlink). Pedicle bone width varies between typically 18 mm for L5 vertebrae to 4.5 mm in T5 vertebrae. Pedicle screw diameters are typically not smaller than 4 mm since their length has to be >25 mm in order to transverse the pedicle and provide enough mechanical support by entering the vertebrae body.

If a 4 mm screw is used on a 5 mm wide pedicle the remaining width on each side is 0.5 mm and the margin for error is <0.5 mm. A system that provides about 0.3 mm accuracy can prevent breach of the bone by the screw.

In this example, the number of pixels of the cameras and projector may be larger than 1200×600 pixels (400 mm×200 mm/0.33 mm), given the FOV and resolution defined above.

The size of subsystem 1100's housing may be determined by the baseline distance between cameras 1102, which in turn is set by the accuracy requirements and depth of field of the system.

Figure 6:
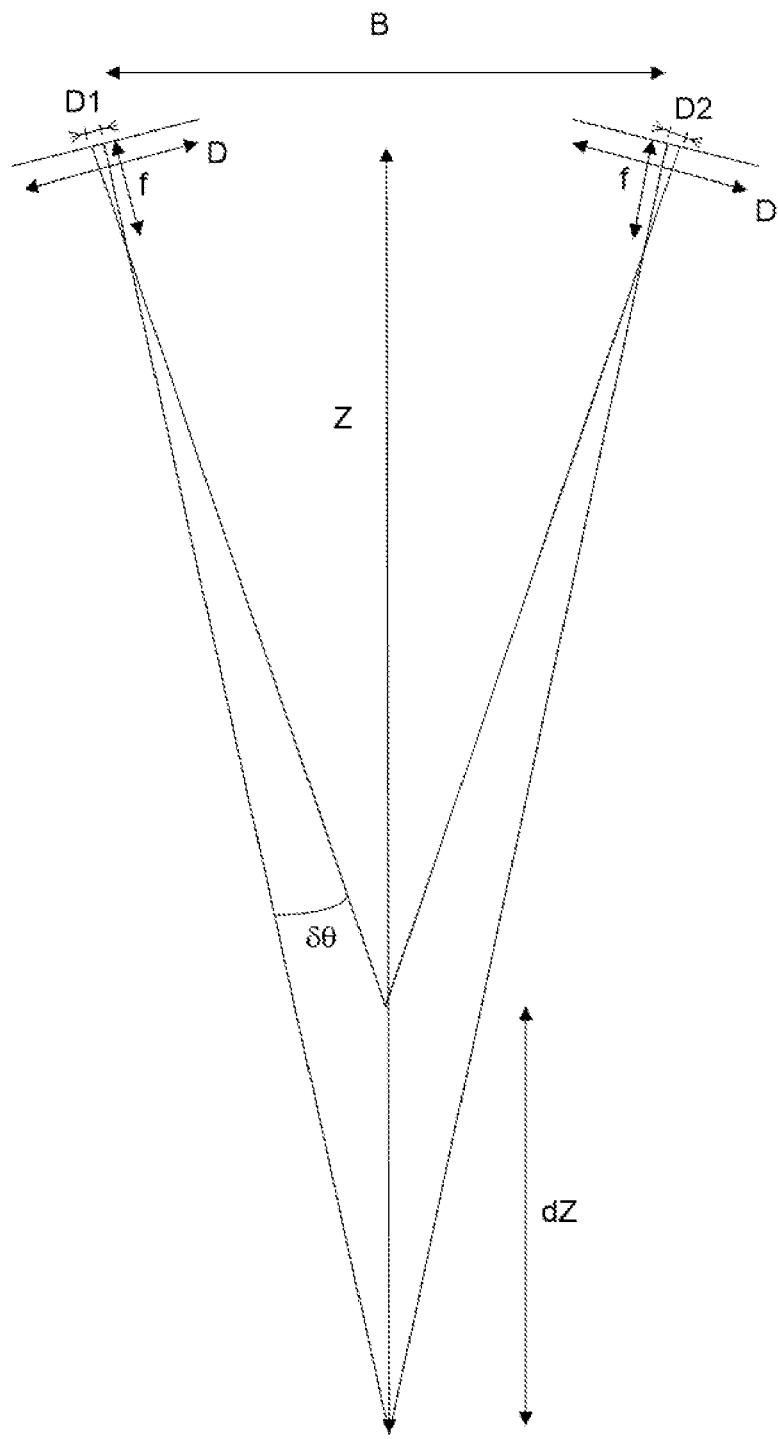
FIG. 6 is a diagram illustrating example design considerations for a camera.

FIG. 6 shows an example arrangement of both cameras and the relevant distances and some possible design considerations.

In FIG. 6, the depth of field is given by dZ, the nominal distance between the camera lens to the spine is Z, and the baseline distance aka "baseline size" aka "baseline" between cameras 1102a, 1102b is B. The 3D depth of each pixel is determined by the offsets of the same pixel between the two cameras 1102a, 1102b—D1 and D2. The camera lens focal length is marked as f.

For nominal distance of Z=1300 mm, focal length of lens f=16 mm, camera resolution 1280×1024 pixels, the Depth of Field (DOF) of each camera 102a, 102b covers the required dZ if the numerical aperture (F #, ratio of lens iris aperture diameter to the focal length) is F #≈5.

The offset between the pixels D1 and D2 should be less than the width of the image sensor. From FIG. 6, $$\frac{D1}{f} = \tan\delta\theta \approx \frac{d\tan\theta/2}{dZ}dZ = -\frac{B}{2Z}\frac{dZ}{Z},$$

and for a target in the middle of the field D2=−D1.

The sensor size D and the baseline size B are determined to keep D=2D1>f*B/Z*dZ/Z.

For example, for a D=5.12 mm wide sensor with 4 micrometer pixel a suitable baseline may be B<2000 mm. Typically, with the above parameters a baseline distance, as wide as can be placed in the operation room (OR) environment, may be employed. Typical baseline size is B=350 mm to 500 mm.

The above computations exemplify a suitable design for the 3D camera. It is recognized that this is but one possible design of cameras; thus a shorter distance to the object and/or different FOV are also possible and may be used in conjunction with spine surgery.

Another parameter pertaining to use of the 3D camera by the surgeon, during surgery, is the latency of obtaining 3D tracking of tools and vertebrae. Since the patient breathes at about 1 cycle per 10 to 20 seconds, the spine may move up to 10 or 20 mm in each breath. Therefore, it is sought to track the vertebrae with an accuracy of 0.3 mm or better, so the 3D camera and associated software, typically are designed to provide, say, at least 60 frames per cycle, or a refresh rate higher than 6 frames per second.

Cameras 1102 may include an IR bandpass glass filter that passes light with wavelength around the structured light wavelength (for example, the filter may pass light whose wavelength falls between 840 nm to 860 nm, given a structured light projector 1101 whose illumination wavelength is 850 nm) and preferentially blocks all other wavelengths, such as visible light. The OR environment is typically lit with high intensity light to enable the surgeon to see the fine details of the surgery. Using light beyond the visible spectrum, such as near IR or IR wavelengths, allows high image contrast even with strong illumination.

It is also beneficial to actively block—e.g. by appropriate filters—light emission from OR lights that falls within the acceptance bandwidth of the optical filter on cameras 1102. This ensures the OR lights do not degrade the image contrast of the 3D camera.

The 3D camera example described above uses 850 NIR light. Other embodiments may use other wavelengths in the NIR, for example 700 nm, 940 nm, or other wavelengths in between 700 nm to 1000 nm detectable by standard or NIR-enhanced CMOS sensors.

The Tool tracker (aka Tool tracking unit) may be characterized by all or any subset of the following:

Part of spine surgery involves insertion of pedicle screws and other parts that are implanted in the patient's spine. Tool tracking enables accurate mapping of the tool to the operational pre-planning and reducing the probability of bone breaching or spinal cord damage during surgery.

The tracking unit's location is tracked by software tracking, e.g. in at least one image which may be generated by the 3D camera/s, of specific features e.g. fiducials or markers. It is appreciated that any specific markers on the tracking unit—balls, fiducials, or any other readily identifiable markers known in the art, may be employed. The markers are typically attached to the tool and/or tool tracker e.g. as shown in FIG. 2, where the tool tracker is typically attached to the tool. The tool and tool tracker may be integrally formed, or the tool tracker may be mounted on legacy tools. For example, The tool tracker aka tracking unit may be fixedly attached to the appropriate surgery tool e.g. a screw guideline inserter, screw driver, etc., or may be snapped on or otherwise securely fastened, usually once per surgery, and may then be detached after surgery is over and discarded, to enable the tool to be sterilized between surgeries.

A fiducial marker or fiducial is a physical object, or digital representation thereof, e.g. grid or ruler with equidistant markings, which is placed in the field of view (or a digital representation thereof is incorporated into e.g. superimposed onto an image of the field of view) of an imaging system; thus the marker appears in the image produced by the imaging system and is used as a reference and/or measure. A fiducial marker may include a physical object placed into or on the subject being imaged.

The location of the tip of the tool is determined by the system's computer using a 3D model of the tool, including the tool tracker attached to it, and the known location and angle of the tool tracker from the tracking unit. 3D models of all surgery tools are provided by their manufacturers, and are included as part of the system software. For example, tool 3D models may be supplied as .stl files. The surgeon may be shown images of the available tools (files) and clicks on the specific tool s/he is going to present to the system. Tracking typically starts when the system recognizes the tool in its FOV by identifying the tracking markers on the tool, and, typically, indicates to the surgeon that the tool is tracked e.g. by showing the tool position and/or angle on the monitor.

Unlike passive tool tracking with markers attached to tools, the tool tracker is an active device. It includes an IMU chip (for example, 6 axis MEMS single chip IMU with three accelerometers and three gyros from STMicroElectronics, Bosch, TDK etc.), communications chip (for example ZigBee, Bluetooth Low Energy, proprietary RF, other), charger chip and rechargeable battery or non-rechargeable (single use) battery, and indicator LEDs or screen. The tool tracker typically sends, typically continuously, the IMU measured accelerations and rotations to the system computer e.g. via the communications chip. This information may be combined by the tracking software with the tool tracker location and/or angle information obtained from the 3D camera. In instances where the tool tracker viewing by the 3D camera is obstructed—for example, by the surgeon's head or arms— the IMU data may continue to provide information for continuous tracking of the angle and position of the tool.

Figure 7B:
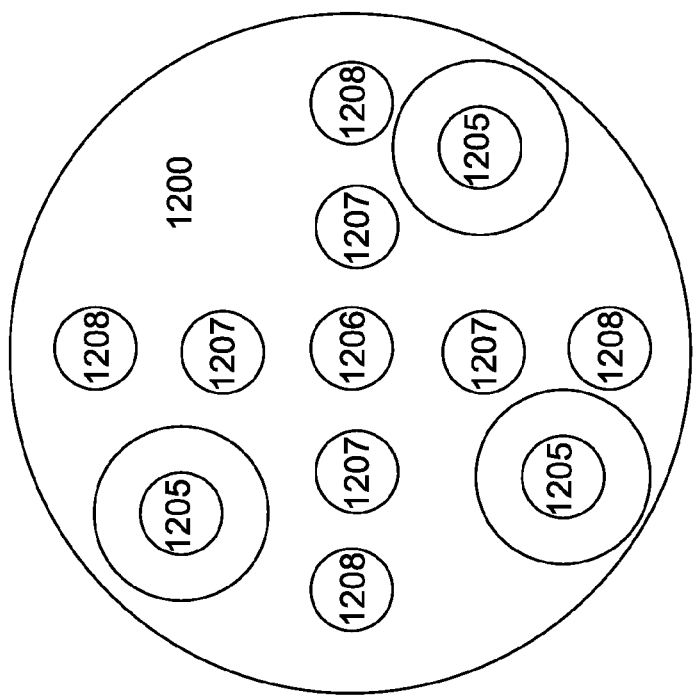
FIGS. 7a, 7b are diagrams of a tool tracker, aka tool adapter.
Figure 7A:
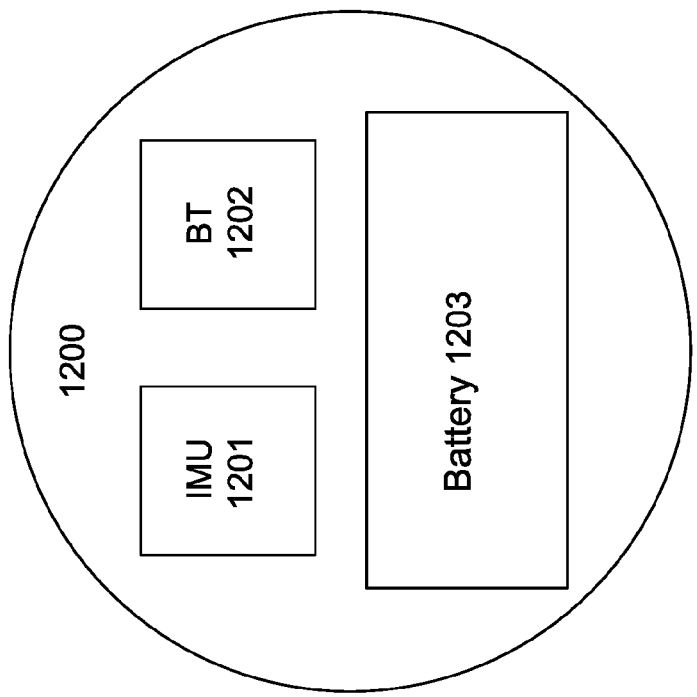

An example of internal and external design of the tool tracker is shown in FIGS. 7a and 7b respectively, which are semi-block diagram semi-pictorial illustrations.

Tool tracker 1200 internally includes IMU chip 1201, communications chip 1202, and battery 1203. Externally the example shows an indicator array of colored LEDs 1206, 1207, 1208, used to display or otherwise present, to the surgeon, feedback angular information, sent back from the computer to the tool 1200, and a set of fiducial markers 1205 for tracking by the 3D camera. Any conventional procedure may be used to perform fiducial tracking using markers. An example of an open source fiducial tracking package is given in: docs.opencv.org/3.1.0/d5/dae/tutorial aruco detection-.html—using OpenCV for detection and tracking of ArUco markers.

For example, the center LED 1206 light changes from Red to Yellow to Green when the tilt angles of the unit are off, close to design angles and equal to design angles, respectively.

The external LEDs e.g. 1207, 1208 light up according to the correction which would yield the desired angle stipulated in the pre-operational planning (aka design angle), with the most peripheral LEDs 1208 being indicative of larger correction, inner LEDs 1207 indicating smaller correction, and only center LED 1206 is indicative of no correction needed. This feedback allows the surgeon to keep his/her eyes on the patient (rather than looking away at a screen out of his field of view, which may conventionally be used to display tool positioning information) and still know how to hold the tool such that the inserted screw (say) will be at the correct pre-planning angle.

The surgeon's feedback example above describes LEDs being used as indicators for feedback. Alternatively or in addition, audio feedback, tactile feedback, screen feedback, or various combinations of the above, may be employed.

The continuous communications between the tool tracker and the computer allows setting of the desired angle stipulated in the pre-operational planning or to change the plan during surgery.

The IMU measurement of tilts and rotations gives two additional capabilities:
1. Measurement of a tool's angular orientation by measuring tilt angles vs. gravity. The tracking unit has to be near the top part of the tool, as to be seen by the surgeon and the 3D camera and also does not interfere with the surgery. This relatively large distance (a typical tool may be 10 cm to 20 cm long) limits the accuracy of the tool angle measurement by the 3D camera. The IMU provides continuous measurement of the tool tilt angles that enhances the tool tip estimate.
2. Tool angle feedback information or estimation of a tool's angular orientation continues to be provided, even while the surgeon's head or any other object blocks the 3D camera's view of the tool. The communications channel keeps sending feedback information to the tool and IMU measurements to the computer, allowing the surgeon to focus on the surgery itself.

The tool tracker implementation of FIG. 7b shows a circular design. However, alternatively, the design may be modified e.g. the tool tracker may be shaped as a torus encircling the tool handle, or may be configured to extend along, and to be fixedly attached to, the side of the tool. The LEDs may be otherwise arranged e.g. in a circle or in plural concentric circles rather than in a cross, or may be replaced or augmented with a display, or any other cost-effective feedback.

The design of the tool tracker is made very simple, to allow sterile, single use operation. In this case the battery may be single use battery.

The System computer may be characterized by all or any subset of the following:

The system computer is typically in data communication with all or any subset of the respective controllers or main processors of the 3D camera, tool tracker/s, and surgery display or monitor unit shown in FIG. 1. It may be positioned on a medical tool rack, moveable rack, or external to the OR with appropriate communication channels. The computer shows the surgery pre-planning aka pre-operational planning or "plan" on the surgery monitor or display screen shown in FIG. 1 and accepts user input to alter the plan e.g. using the pre-planning software. Typically, the initial registration of the 3D camera and surgery tools is also shown on the monitor, as are, typically, the tracked positions of the tools during surgery. The computer communicates with the tool trackers in order to receive IMU data and send to the surgeon feedback information (typically presented "on-board" each tool e.g. as described herein with reference to FIG. 7b inter alia) regarding the tracked positions of any or all tools being used during surgery.

The computer also allows presentation of new applications on the monitor, such as, for example, a bone removal application.

It is appreciated that in some spine surgeries the surgeon seeks to remove bone from various body areas, either for use as material for a bone graft in another location for the same patient, or to remove excess bone. In these cases the bone removal application may provide the surgeon with a measure of how much bone s/he has thus far removed.

The software Graphical User Interface (GUI), when the bone removal app is called up, typically provides an exact estimate of the amount of bone removed, as well as the shape of the removed volume. The 3D camera continuously scans the vertebrae and the software continuously compares the bone surface during the bone removal procedure to the bone surface before bone removal starts, and provides the surgeon with a typically ongoing, immediate and accurate measure of the amount and shape of the removed bone, and optionally provides decision support to determine when to stop, or whether and how to change the direction of bone removal. FIG. 8B is a 2D image, which may be displayed to a surgeon end-user of a sample vertebra cross-section before bone removal and the removed space, which may be shown, say, in a different color than the remainder of the bone which was not removed, including depth and width measurements. In each 2D view there are typically two measurements of the bone volume that was removed e.g. as shown in FIG. 8b.

Software components of the system herein may include all or any subset of the following:
  i. Certain embodiments include identification of vertebrae bone features for real time tracking.
  ii. Certain embodiments include extraction of bone features from pre-operational CT.
  iii. Certain embodiments include CT-to-3D camera registration of vertebrae.
  iv. Certain embodiments include continuous individual vertebra-level tracking Typically, registration follows exposure of bone features to be tracked by the surgeon, in the operating theatre, and precedes tracking which is typically continuous. If tracking is lost for some reason, typically registration is repeated and the continuous tracking resumes.

v. Registration of each tool including initial acquisition by 'presenting' it in the camera field of view to start tracking. The initial tool acquisition may include selecting the tool from a tool menu, by just showing the tool in the camera FOV, or using any other prompt to the software.

vi. Certain embodiments include continuous tool tracking e.g. as described herein.

Processes i, ii, iii above are now described in detail, according to certain embodiments.

i. Vertebrae Bone Features for Real Time Tracking

Real time tracking of multiple spine vertebrae typically relies on identification of specific features in each vertebra external bone surface. The input for vertebrae tracking may comprise a pre-operative CT scan from which the vertebrae bone surface can be extracted e.g. as described below. The surgeon selects a set of bone features for tracking during surgery, either during surgery planning or during the surgery. These features typically include areas that have changing curvature. The actual bone surface areas are both typically exposed and 'cleaned' from tissue and blood during surgery, to allow good matching between the 3D image and the CT.

An example of such an area is the top of the spinous process or any other feature selected by the surgeon as "tracking features". This area is typically exposed during surgery, and once the surgeon cleans the area from surrounding tissue and exposes the bone during surgery, that area can serve as a feature for first registration. To do this, the surgeon cleans tissue off those bone features s/he has chosen as tracking features, and marks the "tracking features" on the CT image, for example by selecting the features using computer input on the CT images and/or by tracking or tracing the tip of a surgery tool that the system tracks around the features.

Accurate registration and tracking typically relies on bone features that are as far apart as possible. In the case of spine vertebrae, the natural features to track are edges of the spinous process and/or of lateral process/es e.g. as shown in FIG. 8A.

If one tracks just the spinous process, for example, it may be hard to determine the exact position of the vertebrae with respect to rotation around the top of the spinous process 'axis'. One can limit this undesirable 'freedom' for error, by cleaning and tracking the full area of the spinous process, but this is time consuming, and still leaves relatively large error, as the spinous process is very narrow.

Figure 8A:
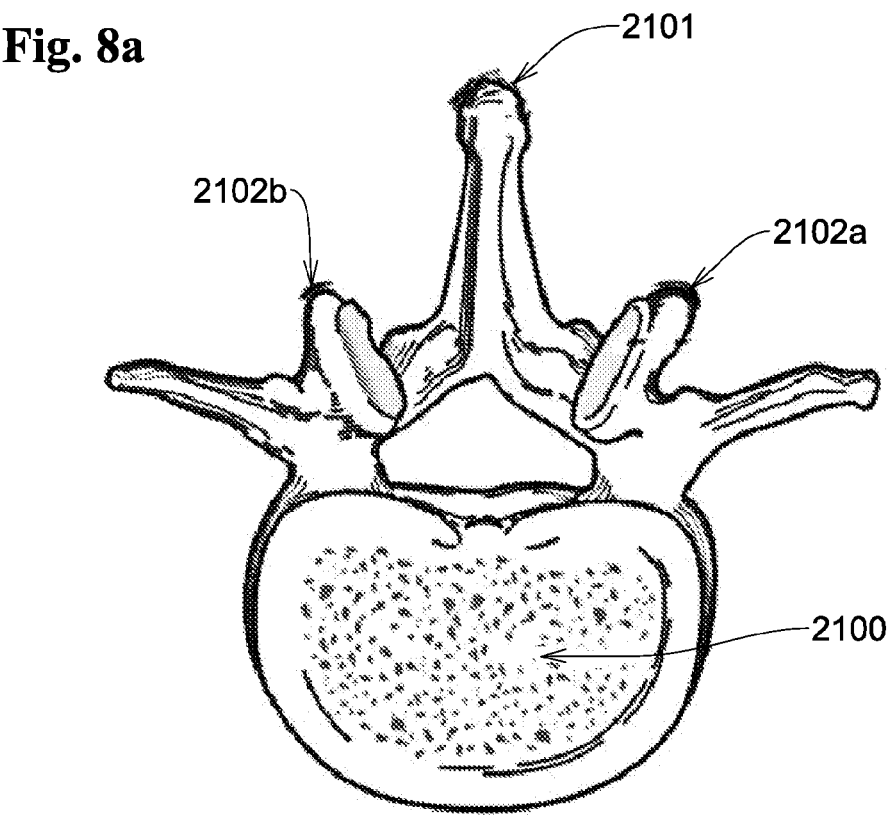
Figure 8B:
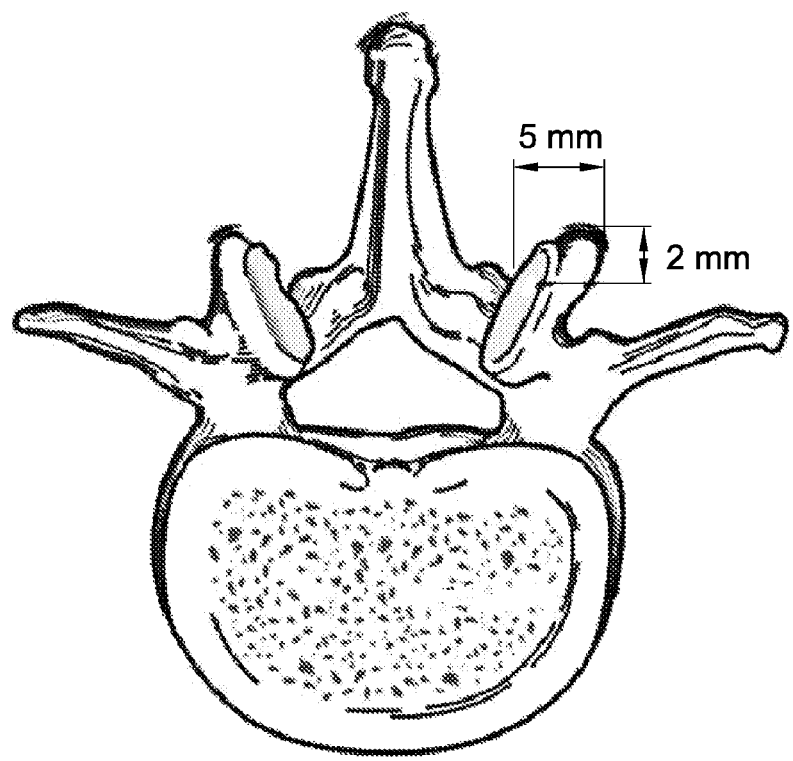

If the surgeon selects top edges (e.g. of the spinous process and of at least one lateral process—referenced 2101 and 2102a, 2102b respectively, in FIG. 8A) as tracking features, this may provide much less 'freedom' for error in estimating the vertebrae position, yet advantageously necessitates cleaning of only a relatively small bone area during surgery. The wide separation between the top edges of the spinous process and the lateral process make for a small position error.

In FIGS. 8a-b, 9a-9c, various views of an example lumbar spine vertebra 2100 are shown; In FIG. 8A the top of the spinous process is marked 2101 and the top of two lateral superior articular processes are marked 2102a and 2102b. The longer side aka 'base' of the triangle formed by the three edges is typically a few cm wide for accurate registration of the vertebrae position and for continuous tracking of the position following initial registration.

Typical dimensions of the vertebrae can be obtained from literature, for example Zhou et. al. "Geometrical Dimensions Of The Lower Lumbar Vertebrae—Analysis Of Data From Digitized CT Images" (available online at: ncbi.nlm-.nih.gov/pmc/articles/PMC3611390/pdf/586_2000_Article_90242.586.pdf). The distance between the top of the two lateral processes typically roughly equals the width of the vertebrae body, and in the adult lumbar spine is typically about 50 mm. The height of the spinous process is typically about 30 mm, yielding an almost equilateral triangle for registration and/or tracking.

If the top of the spinous process and the top of a single lateral process, separated by 40 mm, are used, with an accuracy of registration of, say, 0.3 mm on each end, this yields an estimated angular error of typically only 0.6 degrees. Adding the second lateral process increases the size of the triangle to twice the width and brings the angular error to, typically less than 0.3 degrees since for small angles sin(theta)=theta (in radians).

The example bone features described above are not the only features available for registration and tracking; all or any exposed and cleaned bone areas of the vertebrae may be used for registration; the larger the exposed bone area, the more bone features may be used, and the smaller the error in registration and tracking.

Even cleaning a very small bone area e.g. in the order of a total of 1 cm^2, is typically enough to provide an output which sufficiently supports effective surgery.

ii. Extraction of Bone Features from Pre-Operational CT

Pre-operational planning of surgery typically includes imaging, e.g. taking a CT image of, the patient, analysis of the image to determine which vertebrae will be operated on, and in what way, and planning the surgery.

The CT scan (say) shows cross sections of the body with highlighted—bright—bone areas. The system's CT scan analysis software, e.g. as described below, 'separates' the bone surfaces from the CT and provides a 3D model of the spine vertebrae. In the specific implementation of matching bone features from the CT to the 3D camera image, the software is built to optimize proper recognition and identification of the bone features most usable for tracking—the spinous process and lateral processes. A method for determining bone features from a CT is shown in FIG. 10.

Figure 10:
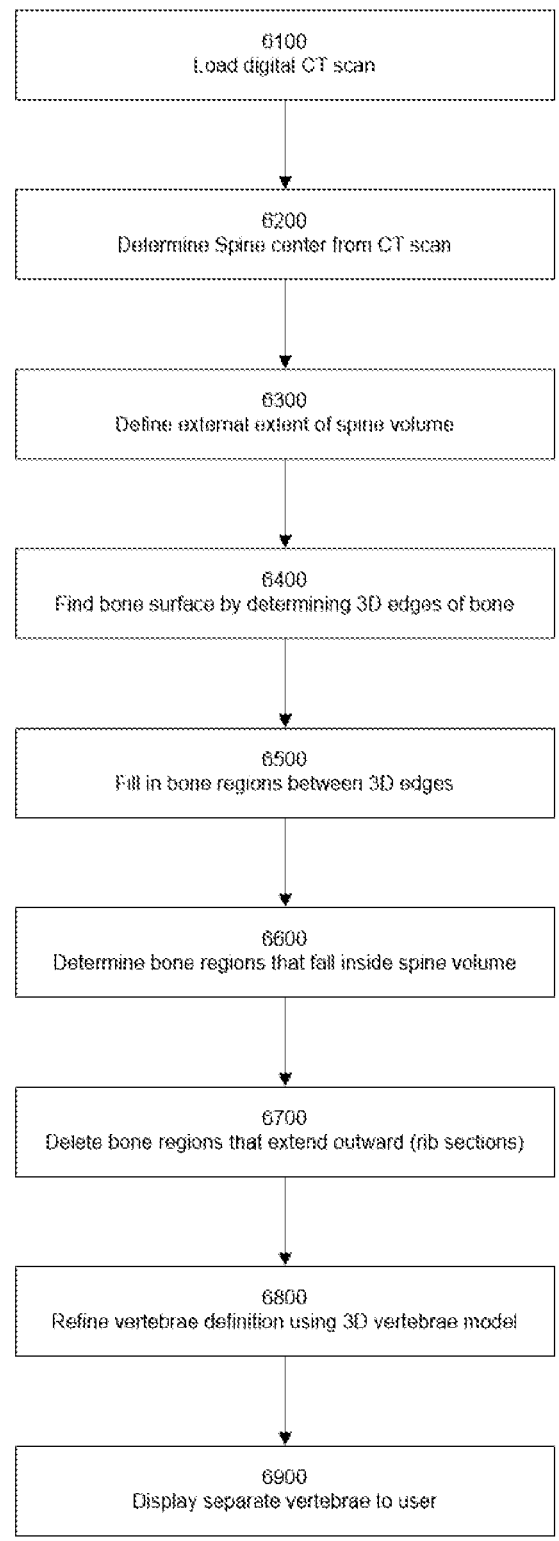
FIG. 10 is a simplified flowchart illustration of a method for extracting bone features from a pre-operative image e.g. CT scan of a spine, which is provided in accordance with an embodiment of the present invention; in this and other flows, all or any subset of the operations may be provided, suitably ordered e.g. as shown.

The bone feature extraction method of FIG. 10 may include all or any subset of the following operations, suitably ordered e.g. as shown:

Operation 6100: Load digital CT scan
Operation 6200: Determine spine centre from CT scan
Operation 6300: Define external extent of spine volume
Operation 6400: Find bone surface by determining 3D edges of bone
Operation 6500: Fill in bone regions between 3D edges
Operation 6600: Determine bone regions that fall inside spine volume
Operation 6700: Delete bone regions that extend outward (rib sections)
Operation 6800: Refine vertebrae definition using 3D vertebrae model
Operation 6900: Display separate vertebrae to user Embodiments of these operations are now described in detail.

Operation 6200: Determine spine center from CT scan—in each slice of a CT scan, the areas that include bone show up as 'brighter' than the areas with soft tissues. Using a Gaussian filter, the fine details are 'smoothed out' and the areas with higher average brightness stand out. Finding the centerline of these areas allows determination of spine center in 3D. In some areas—like the neck, where the spine bones are smaller and the collar bones are thick, the center is determined by extension of the center from lower areas and keeping the deviation between slices smaller than a physical maximum (since the collar bones are relatively far from the spine center).

Operation 6300: Define external extent of spine volume—following the spine center, determine the 'connected' volume around that center. The smoothing Gaussian filter ensures the volume is continuous by smoothing fine details, and also that it extends beyond the extent of the spine. The largest connected volume defines the spine volume. This volume may be used to keep or store only the spine, according to certain embodiments.

Operation 6400: Find bone surface by determining 3D edges of bone—since the bone surface is brighter than the tissue around it, and also the bone center, applying an edge detection algorithm allows determination of the bone surface. By looking for 'edges' along different directions all the 3D bone surfaces 'stand out'. Edge detection in images has a few methods known in the art, such as Canny algorithm, convolution, etc. To minimize spurious edges, the data is first 'de-noised' to remove bright areas that are not connected to the spine center. To highlight the edges, the original CT intensity map may also be 'stretched' by applying a higher Gamma filter.

Operation 6500: Fill in bone regions between 3D edges. First, the bone volume of 'bone' is filled. This can be performed by 'region growing' that first closes any open edges, and then connects regions that are close to each other.

Operation 6600: Determine bone regions that fall inside spine volume. The software automatically detects which bone regions fall inside spine volume e.g. as determined in operation 6300.

Operation 6700: Delete bone regions that extend outward (rib sections). The software discards bone regions that have been found to fall fully or partially outside the spine volume determined in operation 6300. This helps in eliminating the ribs and keeping only the spine.

Operation 6800: Refine vertebrae definition using 3D model. Following determination of the spine from the CT, the spine is typically separated into individual vertebra (segmentation). An a priori vertebrae model helps to separate the bone sections that are part of each vertebra and segment the spine into individual vertebra. The above operations may be implemented using 3D data manipulation software such as for example Open3D and Point Cloud Library (PCL)—libraries of algorithms for point cloud processing tasks and 3D processing, including all or any subset of feature estimation, surface reconstruction, 3D registration, model fitting, and segmentation.

Operation 6900: Display separate vertebrae to user. The display is typically used for pre-planning of surgery.

The method of FIG. 10 is typically performed by the system's central computer, once per surgery, after the CT scan becomes available and before surgery begins. It may also be performed by an application residing on the Internet such as cloud application, or any other suitable method that allows loading of a CT scan, running algorithms on the data, and displaying results to the user.

Segmentation of the spine into separate vertebrae typically requires the use of a priori knowledge of each vertebra shape and relationship to adjacent vertebrae. This knowledge may be supplied in the form of 3D models of the individual vertebra generated by the CT scan analysis software. One way to use a large knowledge base including accumulated "big data" regarding structures of spine vertebrae of many patients, is to build a Neural Network that may 'learn' to segment the separate vertebrae by going over a large database of annotated CT scans.

iii. Registration and Tracking of Individual Vertebrae

Typically, the input to registration includes markings, generated by the surgeon who has cleaned tissue off those bone features s/he has chosen as tracking features and marks the "tracking features" on the CT image and on the spine.

In order to show the surgeon how to execute the pre-surgery planning (typically marked on the CT scan of the patient spine by the software and displayed to the surgeon using the software's user interface), registration is first established, between the pre-operational CT scan and the 3D camera images. The bone features extracted from the CT scan and marked on the image are identified in the 3D camera image. For example, in the scenario of FIG. 1 the surgeon may mark a specific point on the patient's spine with a tool (e.g. the tool 202 in FIG. 2) having tracking markers. The 3D camera tracks the tool tip, and the surgeon may mark the relevant point also on the CT scan data. Marking a few—say 1 or 2 or 4 or 6 or 10-points per vertebra, enables matching the CT scan to the 3D camera image. Typically, the surgeon identifies specific points, areas or traces on each vertebra, both on the CT and by marking them to the camera, for example by placing the tip of a suitable tool to each point or tracing a line on exposed bone area. The software matches the CT with the 3D positions of the points or traces as seen by the camera, and tells the surgeon if there is good registration between the CT and camera image. If the software determines that registration is not "good", the surgeon may repeat the registration, or add additional points, traces or features. For example, the surgeon may clean small bone features as described above from tissue. Using a tracked tool tip, the surgeon can trace the 'clean' bone areas for the 3D camera, and label the same areas on the CT scan using any suitable computer input device. This way the correspondence (e.g. registration between the pre-operational CT scan and at least one 3D camera image generated as surgery begins) between bone features is established, and the 3D image can be registered to the CT scan.

The computer or processor or logic may use a suitable registration algorithm including known 3D point cloud registration methods such as Iterative Closest Point (ICP). When the computer signals it has achieved a "good" registration result, for example with Root Mean Square Error (RMSE) fitness better than, say, 0.5 mm between the CT and 3D points, the surgeon can start the operation and the system may use the registration of the bone features for continuous tracking of each individual vertebra.

The direct continuous tracking of bone features on individual vertebrae typically keeps track of any motion of the vertebrae with respect to the 3D camera, typically including intentional or unintentional motion of the camera with respect to the patient. For example, the surgeon may wish to change the camera position in order to see a different section of the patient's spine, or to move the camera to another location that is better suited for the specific procedure. The camera keeps on tracking the vertebrae during this motion, so there is no 'break' in the surgery and the surgeon can continue seamlessly. This holds for both intentional and unintentional motion of the camera, e.g. as long as the tracked bone features are kept within the camera FOV while the camera is shifted or moved.

During initial registration of the bone features, the surgeon may move the camera intentionally to increase the FOV or to 'see' the spine from additional angles. The camera software is typically configured for 'merging' the set of images acquired during motion, into a single 3D view of the expanded FOV. This feature allows for better initial registration since the camera may use an increased number of points and multiple views to match the CT data. Merging of multiple point cloud images of the same object may be performed, for example, using Open3D package multiway registration code e.g. as described in the online document at the following www location: open3d.org/docs/release/tutorial/Advanced/multiway_registration.html.

Once initial registration of the bone features is achieved, and the camera starts tracking the separate vertebrae, additional image areas around the registered features may be added for tracking. For example, initial registration may only use the 'cleaned' and exposed bone areas to match the CT bone surface. The close perimeter of the 'clean' bone, including tissue, muscle, ligaments, etc. within a radius of, for example, 1 cm from the exposed area, can also be used for tracking, since it is attached to the bone and does not move with respect to it during surgery. This increases the tracked area in the image and enhances the tracking accuracy by allowing tracking of a larger number of 3D image pixels.

A method for surgery planning and/or execution using a computer aided surgery system e.g. any or all of the hardware and software components described herein, is now described. All or any subset of the operations below may be performed, in any suitable order e.g. as shown.

Pre-Operation Planning

This may include all or any subset, in any suitable order, of the following operations:
  i. selection by surgeon of CT scan, loading chosen CT scan into suitable surgery planning software
  ii. showing separate vertebrae and bone features e.g. using bone extraction processes herein
  iii. selecting, by the surgeon, of screws or other implantable devices to be placed during surgery
  iv. placing, by the surgeon, the implantable devices in their planned positions on specific vertebrae using GUI
  v. saving, by the surgeon, of the plan for use during surgery.

The pre-operational planning software typically includes a graphical user interface (GUI) designed e.g. with standard tools to allow the surgeon to go through the above operations i-v. Operation ii typically employs the method of FIG. 10.

The GUI may be characterized by all or any subset of the following features:

According to certain embodiments, when a spine CT is loaded, the original scan may be viewed in 2D and/or 3D views. Typically, a "spine only" option is provided, which, if selected, e.g. clicked results in the processor herein removing background, as well as ribs, vessels and other organs, and displaying only the spine. Typically, a "vertebrae" option is provided which, if selected, e.g. clicked, results in a display of segmented vertebrae typically next to a display of the segmented spine.

Clicking "spine only" may remove the background, and generate only the spine.

Clicking "vertebrae" may show the segmented vertebrae next to the segmented spine. Here the system may show the registration by clicking "scan & register" and starting the camera. Upon clicking finish scan, the registration result may be displayed.

It is appreciated that the GUI may provide all or any subset of the following screen displays to the surgeon end-user:

A main screen may show the patient's name and ID, and surgery identifying particulars e.g. date, name of surgeon etc.

A 2D viewer screen may provide a 2D view of the surgical field e.g. as described herein.

A 2D viewer with angle measurement screen may provide the same, with angular measurements superimposed thereupon.

A 3D viewer may pictorially show a side or isometric view of the spine only, or of the spine and also tool/s and/or screw/s, such that the tool and or screen positions and angular orientations relative to the spine may be viewed by the surgeon.

A scan and registration screen may show the system's progress in scan/registration e.g. as described herein.

A spine only screen is typically provided to allow the surgeon to see the screen without tools, screws, angles and so forth.

A vertebrae screen is typically provided to show a single specific vertebra, e.g. an isometric view thereof and/or various 2D views thereof.

A calibrate screen typically guides the user through calibration e.g. "turn camera on" etc.

An active stage screen may show all or any subset of: an image of the spine, list of screws, options available to surgeon.

It is appreciated that any suitable technique may be performed for importing a patient's data e.g. loading DICOM files that contain the CT scan of the patient or any other digital representation of the patient's spine, typically in association with a patient's meta-data such as patient's name, date of birth, etc.

It is appreciated that a 2D viewer application is typically provided so as to allow the display screen herein to present to a surgeon end-user, a desired 2D view of the CT. Typically, the system supports an addition of annotations to the images which may then be saved and may then be loaded the next time the 2D viewer application is started.

It is appreciated that a 3D viewer application is typically provided so as to allow a 3D view of the CT scan and/or three 2D views (axial, sagittal, coronal). Typically the system supports addition by the user of predefined STL objects e.g. screws and/or tools and manipulation thereof in 3D and the system then displays the change or manipulation, reflected in all views. Typically, the user can also move the objects in the 2D planes. Typically, selecting e.g. clicking on an object automatically sets the slice where that object is located in the 2D views. Typically, the surgeon end user may, e.g. by clicking on an extend button on any of the 2D views, enlarge these views, making them easier to interact. Typically, besides removing the objects, the user may e.g. by clicking a "save position" button, save current positions of objects for re-loading next time the application starts.

Surgery Execution

The process of actually performing surgery in the operating theatre, may include all or any subset, in any suitable order, of the following operations:
  i. selection, by a surgeon, of a pre-operation plan for specific surgery and loading of the plan
  ii. exposure/cleaning by a surgeon, of bone areas on specific vertebrae identified as 'tracking features'
  iii. registration by a system between 3D image of tracking features and a pre-operation CT scan
  iv. continuous tracking by the system of specific vertebrae position during surgery
  v. registration, by the system, of surgery tool/s shown to a 3D camera by the surgeon.

vi. continuous tracking by the system, of surgery tools, typically displaying tools and their location on the CT image, for viewing by the surgeon on a display monitor vii. execution of surgery plan by surgeon—placing implantable devices in patient's spine viii change of plan by the surgeon using pre-operation planning software—available at any time during surgery Another advantage of the surgery execution flow described herein is that the flow typically does not include the use of CT and/or other X-ray modalities such as fluoroscopy. The hardware and algorithms described herein enable the system to assist the surgeon in executing surgery pre-planning without requiring additional radiation exposure during surgery.

It is appreciated that terminology such as "mandatory", "required", "need" and "must" refer to implementation choices made within the context of a particular implementation or application described herewithin for clarity and are not intended to be limiting, since in an alternative implementation, the same elements might be defined as not mandatory and not required, or might even be eliminated altogether.

Components described herein as software may, alternatively, be implemented wholly or partly in hardware and/or firmware, if desired, using conventional techniques, and vice-versa. Each module or component or processor may be centralized in a single physical location or physical device or distributed over several physical locations or physical devices.

Included in the scope of the present disclosure, inter alia, are electromagnetic signals in accordance with the description herein. These may carry computer-readable instructions for performing any or all of the operations of any of the methods shown and described herein, in any suitable order including simultaneous performance of suitable groups of operations as appropriate. Included in the scope of the present disclosure, inter alia, are machine-readable instructions for performing any or all of the operations of any of the methods shown and described herein, in any suitable order; program storage devices readable by machine, tangibly embodying a program of instructions executable by the machine to perform any or all of the operations of any of the methods shown and described herein, in any suitable order i.e. not necessarily as shown, including performing various operations in parallel or concurrently rather than sequentially as shown; a computer program product comprising a computer useable medium having computer readable program code, such as executable code, having embodied therein, and/or including computer readable program code for performing, any or all of the operations of any of the methods shown and described herein, in any suitable order; any technical effects brought about by any or all of the operations of any of the methods shown and described herein, when performed in any suitable order; any suitable apparatus or device or combination of such, programmed to perform, alone or in combination, any or all of the operations of any of the methods shown and described herein, in any suitable order; electronic devices each including at least one processor and/or cooperating input device and/or output device and operative to perform e.g. in software any operations shown and described herein; information storage devices or physical records, such as disks or hard drives, causing at least one computer or other device to be configured so as to carry out any or all of the operations of any of the methods shown and described herein, in any suitable order; at least one program pre-stored e.g. in memory or on an information network such as the Internet, before or after being downloaded, which embodies any or all of the operations of any of the methods shown and described herein, in any suitable order, and the method of uploading or downloading such, and a system including server/s and/or client/s for using such; at least one processor configured to perform any combination of the described operations or to execute any combination of the described modules; and hardware which performs any or all of the operations of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any operation or functionality described herein may be wholly or partially computer-implemented e.g. by one or more processors. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

The system may, if desired, be implemented as a web-based system employing software, computers, routers and telecommunications equipment as appropriate.

Any suitable deployment may be employed to provide functionalities e.g. software functionalities shown and described herein. For example, a server may store certain applications, for download to clients, which are executed at the client side, the server side serving only as a storehouse. Any or all functionalities e.g. software functionalities shown and described herein may be deployed in a cloud environment. Clients e.g. mobile communication devices such as smartphones may be operatively associated with, but external to the cloud.

The scope of the present invention is not limited to structures and functions specifically described herein and is also intended to include devices which have the capacity to yield a structure, or perform a function, described herein, such that even though users of the device may not use the capacity, they are, if they so desire, able to modify the device to obtain the structure or function.

Any "if-then" logic described herein is intended to include embodiments in which a processor is programmed to repeatedly determine whether condition x, which is sometimes true and sometimes false, is currently true or false and to perform y each time x is determined to be true, thereby to yield a processor which performs y at least once, typically on an "if and only if" basis e.g. triggered only by determinations that x is true and never by determinations that x is false.

Any determination of a state or condition described herein, and/or other data generated herein, may be harnessed for any suitable technical effect. For example, the determination may be transmitted or fed to any suitable hardware, firmware or software module, which is known or which is described herein to have capabilities to perform a technical operation responsive to the state or condition. The technical operation may, for example, comprise changing the state or condition, or may more generally cause any outcome which is technically advantageous, given the state or condition or data, and/or may prevent at least one outcome which is disadvantageous given the state or condition or data. Alternatively or in addition, an alert may be provided to an appropriate human operator or to an appropriate external system.

Features of the present invention, including operations, which are described in the context of separate embodiments, may also be provided in combination in a single embodiment. For example, a system embodiment is intended to include a corresponding process embodiment and vice versa. Also, each system embodiment is intended to include a server-centered "view" or client centered "view", or "view" from any other node of the system, of the entire functionality of the system, computer-readable medium, apparatus, including only those functionalities performed at that server or client or node. Features may also be combined with features known in the art and particularly although not limited to those described in the Background section or in publications mentioned therein.

Conversely, features of the invention, including operations, which are described for brevity in the context of a single embodiment or in a certain order may be provided separately or in any suitable subcombination, including with features known in the art (particularly although not limited to those described in the Background section or in publications mentioned therein) or in a different order. "e.g." is used herein in the sense of a specific example which is not intended to be limiting. Each method may comprise all or any subset of the operations illustrated or described, suitably ordered e.g. as illustrated or described herein.

Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, Smart Phone (e.g. iPhone), Tablet, Laptop, PDA, Blackberry GPRS, Satellite including GPS, or other mobile delivery. It is appreciated that in the description and drawings shown and described herein, functionalities described or illustrated as systems and sub-units thereof can also be provided as methods and operations therewithin, and functionalities described or illustrated as methods and operations therewithin can also be provided as systems and sub-units thereof. The scale used to illustrate various elements in the drawings is merely exemplary and/or appropriate for clarity of presentation and is not intended to be limiting.

Any suitable communication may be employed between separate units herein e.g. wired data communication and/or in short-range radio communication with sensors such as cameras e.g. via WiFi, Bluetooth or Zigbee.

It is appreciated that implementation via a cellular app as described herein is but an example and instead, embodiments of the present invention may be implemented, say, as a smartphone SDK, as a hardware component, as an STK application, or as suitable combinations of any of the above.

Any processing functionality illustrated (or described herein) may be executed by any device having a processor, such as but not limited to a mobile telephone, set-top-box, TV, remote desktop computer, game console, tablet, mobile e.g. laptop or other computer terminal, embedded remote unit, which may either be networked itself (may itself be a node in a conventional communication network e.g.) or may be conventionally tethered to a networked device (to a device which is a node in a conventional communication network or is tethered directly or indirectly/ultimately to such a node).

The invention claimed is:

1. A computerized system aiding a surgeon end-user, the system comprising:
    a light projector configured to project at least one pattern onto a spine,
    plural video cameras operative, when the spine is in the camera's field of view, to capture video imagery of the spine and the at least one pattern;
    a tool tracker; and
    a processor including logic configured to receive an output tool-status indication generated by said tool tracker and said video imagery, and to track, with at least millimeter-level accuracy, at least one vertebra of the spine, using said at least one pattern, which is known to the processor, and accordingly to provide feedback with at least millimeter-level accuracy to the surgeon during a surgical procedure, thereby to provide direct tracking of vertebrae rather than of markers attached to the spine,
    said tool tracker comprising:
        an inertial navigation subsystem (INS) to repeatedly compute said output tool-status indication of a current angular orientation and of a current position of at least one tool used during a surgical procedure on the spine, thereby to provide inertial tracking of the at least one tool's position and angle; and
        a wireless communication module operative to provide data communication between said subsystem and said processor including sending said output tool-status indication to the processor,
    wherein Near Infra-Red (NIR) light, having a wavelength to which the plural cameras are responsive, is used to project said at least one pattern,
    wherein at least one of said plural video cameras comprises a filter that
        (i) passes at least said structured light wavelength, and
        (ii) blocks visible light,
    wherein said feedback comprises three-dimensional (3D) depth reconstruction at sub-millimeter accuracy in an operating room lit with visible light by using said NIR light, for projection of said at least one pattern, allowing image contrast high enough to identify the at least one pattern on the video imagery despite illumination, by said visible light, of the operating room,
    wherein the system has software which, based on continuous images of the at least one vertebra, provides continuous individual vertebra-level tracking,
    wherein each position of the at least one tool is continuously tracked,
    and
    wherein the tool tracker's location is tracked by software tracking, in at least one image generated by the plural video cameras.

2. A system according to claim 1 wherein said feedback includes an indication, in real time, of a current relative position and angle of said at least one tool relative to at least a portion of the spine.

3. A system according to claim 1 wherein said feedback comprises visual feedback presented to the surgeon end-user on a display screen which is in data communication with said processor.

4. A system according to claim 1 wherein the tool tracker is mounted on the at least one tool.

5. A system according to claim 4 wherein plural tool trackers are provided, including said tool tracker, and are respectively mounted on plural tools which include said at least one tool, thereby to enable the plural tools to be tracked simultaneously.

6. A system according to claim 1 wherein markers, used for tracking the at least one tool, are fixed to the at least one tool and/or to the tool tracker.

7. A system according to claim 6 wherein said markers comprise fiducial markers.

8. A system according to claim 6 wherein said markers comprise ball markers.

9. A system according to claim 1 and also comprising a user interface via on which the surgeon end-user can mark at least one bone feature to be tracked, on the spine, and wherein the at least one bone feature so marked is used to track at least a portion of the spine.

10. A system according to claim 1 wherein the processor has access to digitally stored a priori knowledge of vertebrae shapes and of geometric relationships between adjacent vertebrae and wherein the processor is configured to segment the spine into individual vertebrae thereby to facilitate tracking of each individual vertebra of the spine.

11. A system according to claim 8 wherein said a priori knowledge comprises at least one three-dimensional (3D) model of at least one of the individual vertebra.

12. A system according to claim 1 wherein the tool tracker presents, to the surgeon end-user, visual feedback, which is generated by the processor, and sent to the tool tracker via said communication module, and which indicates how to change the at least one tool's current angular orientation, by providing feedback including at least one tool position, at least one angular orientation, and at least one depth for the at least one tool, thereby to provide said visual feedback to the surgeon end-user, without requiring the surgeon end-user to look away from a surgical field to view a screen distant from the surgical field.

13. A system according to claim 12 wherein at least one light emitting diode (LED) is mounted on the tool tracker and wherein said at least one LED is controlled to provide said visual feedback.

14. A system according to claim 1 wherein said inertial navigation subsystem (INS) is operative to continually compute output tool-status indications of current angular orientations and current positions of said at least one tool.

15. A system according to claim 1 wherein said filter comprises an infrared (IR) bandpass glass filter.

16. A computer program product, comprising a non-transitory tangible computer readable medium having computer readable program code embodied therein, said computer readable program code adapted to be executed to implement a method comprising the following operations with at least millimeter-level accuracy:
using a tool tracker to repeatedly compute an output tool-status indication of a current angular orientation and of a current position of at least one tool used during a surgical procedure on a spine, thereby to provide inertial tracking of the at least one tool's position and angle; and using a wireless communication module for sending said output tool-status indication to a hardware processor; and
using the hardware processor to receive the output tool-status indication generated by said tool tracker and video imagery generated by plural video cameras, of the spine and of at least one pattern which is projected onto the spine by a light projector and to track at least one vertebra of the spine, using said at least one pattern, which is known to the processor, and accordingly to provide feedback to a surgeon during a surgical procedure on the spine, thereby to provide direct tracking of vertebrae rather than of markers attached to the spine,
wherein Near Infra-Red (NIR) light, having a wavelength to which the plural cameras are responsive, is used to project said at least one pattern,
wherein at least one of said plural video cameras comprises a filter that
(i) passes at least said structured light wavelength, and
(ii) blocks visible light,
wherein said feedback comprises three-dimensional (3D) depth reconstruction at sub-millimeter accuracy in an operating room lit with visible light by using said NIR light, for projection of said at least one pattern, allowing image contrast high enough to identify the at least one pattern on the video imagery despite illumination, by said visible light, of the operating room,
wherein the computer program product has software which, based on continuous imaging of the at least one vertebra, provides continuous individual vertebra-level tracking
where each position of the at least one tool is continuously tracked,
and
wherein the tool tracker's location is tracked by software tracking, in at least one image generated by the plural video cameras.

17. A method aiding a surgeon end-user, the method comprising:
providing a light projector configured to project at least one pattern onto a spine,
providing plural video cameras operative, when the spine is in the cameras' field of view, to capture video imagery of the spine and said at least one pattern;
providing a tool tracker comprising:
an inertial navigation subsystem (INS) constructed and operative to repeatedly compute an output tool-status indication of a current angular orientation and of a current position of at least one tool used during a surgical procedure on the spine, thereby to provide, with at least millimeter-level accuracy, inertial tracking of the at least one tool's position and angle; and
a wireless communication module operative to provide data communication between said subsystem and a processor including sending said output tool-status indication to the processor;
wherein the processor includes logic configured to receive said output tool-status indication generated by said tool tracker and said video imagery, and to track, with at least millimeter-level accuracy, at least one vertebra of the spine, using said at least one pattern, which is known to the processor, and accordingly to provide feedback, with at least millimeter-level accuracy, to the surgeon during a surgical procedure on the spine, thereby to provide direct tracking of vertebrae rather than of markers attached to the spine,
wherein Near Infra-Red (NIR) light, having a wavelength to which the plural cameras are responsive, is used to project said at least one pattern,
wherein at least one of said plural video cameras comprises a filter that
(i) passes at least said structured light wavelength, and
(ii) blocks visible light,
wherein said feedback comprises three-dimensional (3D) depth reconstruction at sub-millimeter accuracy in an operating room lit with visible light by using said NIR light, for projection of said at least one pattern, allowing image contrast high enough to identify the at least one pattern on the video imagery despite illumination, by said visible light, of the operating room, wherein the processor has software which, based on continuous imaging of the at least one vertebra, provides continuous vertebra-level tracking, wherein each position of the at least one tool is continuously tracked, and wherein the tool tracker's location is tracked by software tracking, in at least one image generated by the plural video cameras.

18. A method according to claim 17 wherein directional feedback is provided as the surgeon navigates the at least one tool to align with a pre-planned trajectory.

19. A method according to claim 18 wherein the directional feedback comprises illumination that directs the surgeon to the pre-planned trajectory and position including arrows lit to direct changes that the surgeon needs to make in the at least one tool's position and/or angle as the surgeon navigates the at least one tool.

20. A method according to claim 18 wherein the directional feedback comprises a "traffic-light" Light Emitting Diode (LED) which is green on at least one occasion when the tool is on target and red on at least one occasion when the tool is off target.

* * * * *